(12) United States Patent
Garimella et al.

(10) Patent No.: US 7,485,470 B2
(45) Date of Patent: Feb. 3, 2009

(54) METHOD FOR ATTACHMENT OF SILYLATED MOLECULES TO GLASS SURFACES

(75) Inventors: Viswanadham Garimella, Vernon Hills, IL (US); Yasmith Bernal, Lake Zurich, IL (US)

(73) Assignee: Nanosphere, Inc., Northbrook, IL (US)

( * ) Notice: Subject to any disclaimer, the term of this patent is extended or adjusted under 35 U.S.C. 154(b) by 184 days.

(21) Appl. No.: 11/656,303

(22) Filed: Jan. 19, 2007

(65) Prior Publication Data
US 2007/0141615 A1 Jun. 21, 2007

Related U.S. Application Data

(62) Division of application No. 10/447,073, filed on May 28, 2003, now Pat. No. 7,297,553.

(60) Provisional application No. 60/383,564, filed on May 28, 2002.

(51) Int. Cl.
G01N 33/543 (2006.01)
G01N 33/551 (2006.01)
G01N 33/552 (2006.01)
G01N 33/00 (2006.01)
C12Q 1/00 (2006.01)
C12Q 1/68 (2006.01)
C12N 11/00 (2006.01)

(52) U.S. Cl. ............ 436/518; 436/524; 436/527; 436/106; 436/109; 436/127; 435/4; 435/6; 435/174

(58) Field of Classification Search ............ 436/518, 436/524, 527, 106, 109; 435/4, 6, 174
See application file for complete search history.

(56) References Cited

U.S. PATENT DOCUMENTS

| | | | |
|---|---|---|---|
| 4,059,685 A | 11/1977 | Johnson | |
| 4,067,959 A | 1/1978 | Bolz | |
| 4,275,149 A | 6/1981 | Litman et al. | |
| 4,751,177 A | 6/1988 | Stabinsky | |
| 4,797,355 A | 1/1989 | Stabinsky | |
| 4,824,776 A | 4/1989 | Heller | |
| 4,847,159 A | 7/1989 | Glajch et al. | |
| 4,853,335 A | 8/1989 | Olsen et al. | |

(Continued)

FOREIGN PATENT DOCUMENTS

EP 0 245 206 A1 11/1987

(Continued)

OTHER PUBLICATIONS

Beck C., et al., "Covalent surface functionalization and self-organization of silica nanoparticles," *Angew .Chem. Int. Ed*, vol. 38, No. 9, p. 1297-1300 (1999).

(Continued)

*Primary Examiner*—Jezia Riley
(74) *Attorney, Agent, or Firm*—Gregory T. Pletta

(57) ABSTRACT

A method for the efficient immobilization of silylated molecules such as silylated oligonucleotides or proteins onto unmodified surfaces such as a glass surface is provided. Also provided are compounds, devices, and kits for modifying surfaces such as glass surfaces.

4 Claims, 6 Drawing Sheets

U.S. PATENT DOCUMENTS

| | | | |
|---|---|---|---|
| 4,877,745 A | 10/1989 | Hayes et al. |
| 4,886,741 A | 12/1989 | Schwartz |
| 5,057,301 A | 10/1991 | Wilbur et al. |
| 5,071,978 A | 12/1991 | San |
| 5,109,124 A | 4/1992 | Ramachandran et al. |
| 5,114,674 A | 5/1992 | Stanbro et al. |
| 5,124,246 A | 6/1992 | Urdea et al. |
| 5,143,854 A | 9/1992 | Pirrung et al. |
| 5,233,369 A | 8/1993 | Carlotta et al. |
| 5,314,731 A | 5/1994 | Yoneda et al. |
| 5,324,633 A | 6/1994 | Fodor et al. |
| 5,342,867 A | 8/1994 | Ryan et al. |
| 5,399,501 A | 3/1995 | Pope et al. |
| 5,482,867 A | 1/1996 | Barrett et al. |
| 5,486,855 A | 1/1996 | Carlotta et al. |
| 5,514,785 A | 5/1996 | Van Ness et al. |
| 5,527,673 A | 6/1996 | Reinhartz et al. |
| 5,532,170 A | 7/1996 | Buckle et al. |
| 5,567,294 A | 10/1996 | Dovichi et al. |
| 5,567,295 A | 10/1996 | Swamy et al. |
| 5,585,275 A | 12/1996 | Hudson et al. |
| 5,591,646 A | 1/1997 | Hudson et al. |
| 5,599,695 A | 2/1997 | Pease et al. |
| 5,622,826 A | 4/1997 | Varma |
| 5,624,711 A | 4/1997 | Sundberg et al. |
| 5,631,734 A | 5/1997 | Stern et al. |
| 5,690,894 A | 11/1997 | Pinkel et al. |
| 5,717,083 A | 2/1998 | Cook |
| 5,770,456 A | 6/1998 | Holmes |
| 5,773,308 A | 6/1998 | Conrad et al. |
| 5,831,070 A | 11/1998 | Pease et al. |
| 5,837,196 A | 11/1998 | Pinkel et al. |
| 5,837,454 A | 11/1998 | Cozzette |
| 5,840,190 A | 11/1998 | Scholander et al. |
| 5,858,653 A | 1/1999 | Duran et al. |
| 5,868,936 A | 2/1999 | Ofsthun et al. |
| 5,871,649 A | 2/1999 | Ofsthun et al. |
| 5,919,523 A | 7/1999 | Sundberg et al. |
| 5,959,098 A | 9/1999 | Goldberg et al. |
| 6,004,752 A | 12/1999 | Loewy et al. |
| 6,004,755 A | 12/1999 | Wang |
| 6,013,440 A | 1/2000 | Lipshutz et al. |
| 6,040,138 A | 3/2000 | Lockhart et al. |
| 6,045,996 A | 4/2000 | Cronin et al. |
| 6,080,585 A | 6/2000 | Southern et al. |
| 6,101,946 A | 8/2000 | Martinsky |
| 6,103,474 A | 8/2000 | Dellinger et al. |
| 6,124,102 A | 9/2000 | Fodor et al. |
| 6,136,269 A | 10/2000 | Winkler et al. |
| 6,140,044 A | 10/2000 | Besemer et al. |
| 6,141,096 A | 10/2000 | Stern et al. |
| 6,146,593 A | 11/2000 | Pinkel et al. |
| 6,150,103 A | 11/2000 | Ness et al. |
| 6,150,147 A | 11/2000 | Goldberg et al. |
| 6,153,743 A | 11/2000 | Hubbell et al. |
| 6,174,683 B1 | 1/2001 | Hahn et al. |
| 6,180,942 B1 | 1/2001 | Tracy et al. |
| 6,203,989 B1 | 3/2001 | Goldberg et al. |
| 6,225,625 B1 | 5/2001 | Pirrung et al. |
| 6,239,273 B1 | 5/2001 | Pease et al. |
| 6,248,127 B1 | 6/2001 | Shah et al. |
| 6,261,776 B1 | 7/2001 | Pirrung et al. |
| 6,262,216 B1 | 7/2001 | McGall |
| 6,271,957 B1 | 8/2001 | Quate et al. |
| 6,274,384 B1 | 8/2001 | Starzl et al. |
| 6,280,950 B1 | 8/2001 | Lipshutz et al. |
| 6,284,465 B1 | 9/2001 | Wolber et al. |
| 6,284,497 B1 | 9/2001 | Sabanayagam et al. |
| 6,291,183 B1 | 9/2001 | Pirrung et al. |
| 6,294,324 B1 | 9/2001 | Bensimon et al. |
| 6,306,584 B1 | 10/2001 | Bamdad |
| 6,309,824 B1 | 10/2001 | Drmanac |
| 6,309,828 B1 | 10/2001 | Schleifer et al. |
| 6,319,674 B1 | 11/2001 | Fulcrand et al. |
| 6,326,489 B1 | 12/2001 | Church et al. |
| 6,329,143 B1 | 12/2001 | Stryer et al. |
| 6,361,944 B1 | 3/2002 | Mirkin et al. |
| 6,383,742 B1 | 5/2002 | Drmanac et al. |
| 6,383,749 B2 | 5/2002 | Bochkariov et al. |
| 6,399,365 B2 | 6/2002 | Besemer et al. |
| 6,403,317 B1 | 6/2002 | Anderson |
| 6,403,957 B1 | 6/2002 | Fodor et al. |
| 6,406,844 B1 | 6/2002 | Pirrung et al. |
| 6,406,921 B1 | 6/2002 | Wagner et al. |
| 6,410,229 B1 | 6/2002 | Lockhart et al. |
| 6,410,675 B2 | 6/2002 | McGall et al. |
| 6,417,340 B1 | 7/2002 | Mirkin et al. |
| 6,417,506 B1 | 7/2002 | Pinkel et al. |
| 6,429,275 B2 | 8/2002 | McGall et al. |
| 6,440,677 B2 | 8/2002 | Lipshutz et al. |
| 6,448,010 B1 | 9/2002 | Zhao |
| 6,458,533 B1 | 10/2002 | Felder et al. |
| 6,465,178 B2 | 10/2002 | Chappa et al. |
| 6,475,440 B1 | 11/2002 | Bochkariov |
| 6,475,808 B1 | 11/2002 | Wagner et al. |
| 6,475,809 B1 | 11/2002 | Wagner et al. |
| 6,480,324 B2 | 11/2002 | Quate et al. |
| 6,482,593 B2 | 11/2002 | Walt et al. |
| 6,486,287 B2 | 11/2002 | McGall et al. |
| 6,489,160 B2 | 12/2002 | Hashimoto |
| 6,498,010 B1 | 12/2002 | Fitzgerald et al. |
| 6,506,895 B2 | 1/2003 | Guire et al. |
| 6,511,849 B1 | 1/2003 | Wang |
| 6,514,768 B1 | 2/2003 | Guire et al. |
| 6,548,021 B1 | 4/2003 | Church et al. |
| 6,548,257 B2 | 4/2003 | Lockhart et al. |
| 6,548,263 B1 | 4/2003 | Kapur et al. |
| 6,548,652 B2 | 4/2003 | Lukhtanov et al. |
| 6,551,817 B2 | 4/2003 | Besemer et al. |
| 6,562,136 B1 | 5/2003 | Chappa et al. |
| 6,569,671 B1 | 5/2003 | Okamoto et al. |
| 6,579,463 B1 | 6/2003 | Winningham et al. |
| 6,579,719 B1 | 6/2003 | Hutchens et al. |
| 6,589,778 B1 | 7/2003 | Hawkins |
| 6,605,363 B2 | 8/2003 | Ho et al. |
| 6,617,125 B2 | 9/2003 | Adler, Jr. |
| 6,621,553 B2 | 9/2003 | Baxter et al. |
| 6,630,308 B2 | 10/2003 | Stryer et al. |
| 6,630,358 B1 | 10/2003 | Wagner et al. |
| 6,632,605 B1 | 10/2003 | Cronin et al. |
| 6,646,243 B2 | 11/2003 | Pirrung et al. |
| 6,660,234 B2 | 12/2003 | Stryer et al. |
| 6,667,394 B2 | 12/2003 | Pease et al. |
| 6,680,178 B2 | 1/2004 | Harris et al. |
| 6,703,498 B2 | 3/2004 | Tchaga |
| 6,706,408 B2 | 3/2004 | Jelle |
| 6,709,712 B2 | 3/2004 | Chappa et al. |
| 6,713,262 B2 | 3/2004 | Gellibolian et al. |
| 6,733,894 B2 | 5/2004 | Ho et al. |
| 6,733,977 B2 | 5/2004 | Besemer et al. |
| 6,741,344 B1 | 5/2004 | Stern et al. |
| 6,743,630 B2 | 6/2004 | Sato |
| 6,743,882 B2 | 6/2004 | McGall et al. |
| 6,747,143 B2 | 6/2004 | Stryer et al. |
| 6,753,145 B2 | 6/2004 | Holcomb et al. |
| 6,756,232 B2 | 6/2004 | Schermer et al. |
| 6,762,019 B2 | 7/2004 | Swan et al. |
| 6,773,676 B2 | 8/2004 | Schembri |
| 6,773,888 B2 | 8/2004 | Li et al. |
| 6,777,239 B2 | 8/2004 | Dower et al. |
| 6,784,982 B1 | 8/2004 | Blumenfeld et al. |
| 6,794,197 B1 | 9/2004 | Indermuhle et al. |
| 6,797,393 B2 | 9/2004 | Qiao et al. |
| 6,800,849 B2 | 10/2004 | Staats |

| | | |
|---|---|---|
| 6,806,047 B2 | 10/2004 | Goldberg et al. |
| 6,806,050 B2 | 10/2004 | Zhou et al. |
| 6,808,908 B2 | 10/2004 | Yao et al. |
| 6,811,969 B1 | 11/2004 | Hutchens et al. |
| 6,818,394 B1 | 11/2004 | O'Donnell-Maloney et al. |
| 6,818,411 B2 | 11/2004 | Hutchens et al. |
| 6,828,104 B2 | 12/2004 | Lipshutz et al. |
| 6,828,110 B2 | 12/2004 | Lee et al. |
| 6,844,165 B2 | 1/2005 | Hutchens et al. |
| 6,849,462 B1 | 2/2005 | Winkler et al. |
| 6,852,393 B2 | 2/2005 | Gandon |
| 6,855,490 B2 | 2/2005 | Sompuram et al. |
| 6,855,501 B2 | 2/2005 | Huang |
| 2001/0031468 A1 | 10/2001 | Chenchick et al. |
| 2001/0031469 A1 | 10/2001 | Volinia |
| 2001/0041249 A1 | 11/2001 | Patron et al. |
| 2001/0053521 A1 | 12/2001 | Kramer et al. |
| 2002/0001834 A1 | 1/2002 | Keogh et al. |
| 2002/0019015 A1 | 2/2002 | Lahiri et al. |
| 2002/0042048 A1 | 4/2002 | Drmanac |
| 2002/0072127 A1 | 6/2002 | Sofield et al. |
| 2002/0075490 A1 | 6/2002 | Chappell |
| 2002/0076716 A1 | 6/2002 | Sabanayagam et al. |
| 2002/0076727 A1 | 6/2002 | Cardone et al. |
| 2002/0094544 A1 | 7/2002 | Fang et al. |
| 2002/0106702 A1 | 8/2002 | Wagner et al. |
| 2002/0137090 A1 | 9/2002 | Pinkel et al. |
| 2002/0142351 A1 | 10/2002 | Diamond |
| 2002/0155442 A1 | 10/2002 | Mirkin et al. |
| 2002/0164656 A1 | 11/2002 | Hoeffler et al. |
| 2003/0013130 A1 | 1/2003 | Charych et al. |
| 2003/0027154 A1 | 2/2003 | Narahara et al. |
| 2003/0027298 A1 | 2/2003 | Bott et al. |
| 2003/0032035 A1 | 2/2003 | Chatelain et al. |
| 2003/0036095 A1 | 2/2003 | Tchaga |
| 2003/0040129 A1 | 2/2003 | Shah |
| 2003/0044801 A1 | 3/2003 | Harvey |
| 2003/0059094 A1 | 3/2003 | Cattell et al. |
| 2003/0068621 A1 | 4/2003 | Briggs |
| 2003/0099930 A1 | 5/2003 | Graves et al. |
| 2003/0138853 A1 | 7/2003 | Lahiri et al. |
| 2003/0143542 A1 | 7/2003 | Qiao et al. |
| 2003/0143576 A1 | 7/2003 | Chao et al. |
| 2003/0148360 A1 | 8/2003 | Guire et al. |
| 2003/0166261 A1 | 9/2003 | Sompuram et al. |
| 2003/0170914 A1 | 9/2003 | Guire et al. |
| 2003/0180957 A1 | 9/2003 | Koopmann et al. |
| 2003/0186252 A1 | 10/2003 | Ilsley et al. |
| 2003/0186310 A1 | 10/2003 | Kincaid et al. |
| 2003/0198967 A1 | 10/2003 | Matson et al. |
| 2003/0215806 A1 | 11/2003 | Lewis et al. |
| 2003/0215841 A1 | 11/2003 | Lockhart et al. |
| 2003/0215856 A1 | 11/2003 | Church et al. |
| 2003/0231987 A1 | 12/2003 | Carmack et al. |
| 2004/0002078 A1 | 1/2004 | Boutell et al. |
| 2004/0018523 A1 | 1/2004 | Hawkins et al. |
| 2004/0029303 A1 | 2/2004 | Hart et al. |
| 2004/0063220 A1 | 4/2004 | Lebrun et al. |
| 2004/0073017 A1 | 4/2004 | Skrzypcznski et al. |
| 2004/0076961 A1 | 4/2004 | Lewis et al. |
| 2004/0096856 A1 | 5/2004 | Garimella et al. |
| 2004/0096914 A1 | 5/2004 | Fang et al. |
| 2004/0101838 A1 | 5/2004 | Thomspon et al. |
| 2004/0106131 A1 | 6/2004 | Roy et al. |
| 2004/0132080 A1 | 7/2004 | Kawaguchi et al. |
| 2004/0137493 A1 | 7/2004 | Goldberg et al. |
| 2004/0142095 A1 | 7/2004 | Narahara et al. |
| 2004/0161748 A1 | 8/2004 | He et al. |
| 2004/0175717 A1 | 9/2004 | Van Zyle et al. |
| 2004/0185451 A1 | 9/2004 | Leproust et al. |
| 2004/0185464 A1 | 9/2004 | Kris et al. |
| 2004/0185473 A1 | 9/2004 | Cuppoletti et al. |
| 2004/0191813 A1 | 9/2004 | Bruhn et al. |
| 2004/0206902 A1 | 10/2004 | Staats et al. |
| 2004/0209383 A1 | 10/2004 | Yin et al. |
| 2004/0214019 A1 | 10/2004 | McGall et al. |
| 2004/0215031 A1 | 10/2004 | McGall et al. |
| 2004/0224326 A1 | 11/2004 | Kim et al. |
| 2004/0229287 A1 | 11/2004 | Sato et al. |
| 2004/0234788 A1 | 11/2004 | Li et al. |
| 2004/0241663 A1 | 12/2004 | Peck et al. |
| 2004/0241666 A1 | 12/2004 | Amorese et al. |
| 2004/0241668 A1 | 12/2004 | Amorese et al. |
| 2004/0241742 A1 | 12/2004 | Peck et al. |
| 2004/0241880 A1 | 12/2004 | Leproust et al. |
| 2004/0248162 A1 | 12/2004 | Cuppoletti et al. |
| 2004/0248323 A1 | 12/2004 | Zhou et al. |
| 2004/0253460 A1 | 12/2004 | McGall et al. |
| 2004/0253640 A1 | 12/2004 | Chen et al. |
| 2004/0265813 A1 | 12/2004 | Takechi et al. |
| 2005/0003395 A1 | 1/2005 | Gellibolian et al. |
| 2005/0008674 A1 | 1/2005 | Wagner et al. |
| 2005/0014292 A1 | 1/2005 | Wagner et al. |
| 2005/0032060 A1 | 2/2005 | Shah et al. |

FOREIGN PATENT DOCUMENTS

| | | |
|---|---|---|
| EP | 0 628 568 | 6/1994 |
| EP | 1 001 267 | 5/2000 |
| WO | WO 91/00288 A1 | 1/1991 |
| WO | WO 98/04740 | 2/1998 |
| WO | WO 99/04896 | 2/1999 |
| WO | WO 01/00876 | 1/2001 |
| WO | WO 01/46213 | 6/2001 |
| WO | WO 01/46214 | 6/2001 |
| WO | WO 01/46464 | 6/2001 |
| WO | WO 01/51665 | 7/2001 |
| WO | WO 01/51689 | 7/2001 |
| WO | WO 01/98458 | 12/2001 |
| WO | WO 02/06384 | 1/2002 |
| WO | WO 03/006676 | 7/2002 |
| WO | WO 02/096979 | 12/2002 |

OTHER PUBLICATIONS

Beier M., et al., "Versatile derivatisation of solid support media for covalent bonding on DNA-microchips," *Nucleic Acids Research*, vol. 27, p. 1970-1977 (1999).

Chrisey L., et al., "Covalent attachment of synthetic DNA to self-assembled monolayer films," *Nucleic Acids Research*, vol. 24, p. 3031-3039 (1996).

Chrisey L., et al., "Fabrication of patterned DNA surfaces," *Nucleic Acids Research*, vol. 24, p. 3040-3047 (1996).

Frens, G., "Controlled Nucleation for the Regulation of the Particle Size in Monodisperse Gold Suspensions," *Nature Physical Science*, vol. 241, p. 20-22 (1973).

Eckstein, F. (ed.) *Oligonucleotides and Analogues: A Practical Approach* (IRL Press, Oxford, 1991), pp. vii-xvii.

Grabar K., et al., "Preparation and characterization of au colloid monolayers," *Analytical Chemistry*, vol. 67, p. 735-743 (1995).

Guo Z., et al., "Direct fluorescence analysis of genetic polymorphism by hybridization with oligonucleotide arrays on glass supports," *Nucleic Acids Research*, vol. 22, p. 5456-5465 (1994).

Letsinger R., et al., "Use of a steroid cyclic disulfide anchor in constructing gold nanoparticle-oligonucleotide conjugates," *Bioconjugate Chem*, vol. 11, p. 289-291 (2000).

Zammateo N., et al., "Comparison between different strategies of covalent attachment of DNA to glass surfaces to build DNA microarrays," *Analytical biochemistry*, vol. 280, p. 143-150 (2000).

Zhao X., et al., "Immobilization of oligodeoxyribonucleotides with multiple anchors to microchips," *Nucleic Acids Research*, vol. 29, p. 955-959 (2001).

Guo et al., "Direct fluorescence analysis of genetic polymorphisms by hybridization with oligonucleotide arrays on glass supports", *Nucleic Acids Research*, vol. 22, No. 24, pp. 5456-5465 (1994).

Chrisey et al., "Covalent attachment of synthetic DNA to self-assembled monolayer films", *Nucleic Acids Research*, vol. 24, No. 15, pp. 3031-3039 (1996).

Chrisey et al., "Fabrication of patterned DNA surfaces", *Nucleic Acids Research*, vol. 24, No. 15, pp. 3040-3047 (1996).

Beier et al., "Versatile derivatisation of solid support media for covelent bonding on DNA-microchips", *Nucleic Acids Research*, vol. 27, No. 9, pp. 1970-1977 (1999).

Beck et al., "Covalent Surface Functionalization and Self-Organization of Silica Nanoparticles", *Angew. Chem. Int. Ed.*, vol. 38, No. 9, pp. 1297-1300 (1999).

Zammatteo et al., "Comparison between Different Strategies of Covalent Attachment of DNA to Glass Surfaces to Build DNA Microarrays", *Analytical Biochemistry*, vol. 280, pp. 143-150 (2000).

Kumar et al., "Silanized nucleic acids: a general platform for DNA immobilization", *Nucleic Acids Research*, vol. 28, No. 14, pp. E71 i-vi (2000).

Zhao et al., "Immobilization of oligodeoxyribonucleotides with multiple anchors to microchips", *Nucleic Acids Research*, vol. 29, No. 4, pp. 955-959 (2001).

Lindroos et al., "Minisequencing on oligonucleotide microarrays: comparison of immobilization chemistries", *Nucleic Acids Research*, vol. 29, No. 13, pp. E69 1-7 (2001).

Letsinger et al., "Use of a Steroid Cyc;ic Disulfide Anchor in Constructing Gold Nanoparticle-Oligonucleotide Conjugates", *Bioconjugate Chemistry*, vol. 11, pp. 289-291 (2000).

Grabar et al., "Preparation and Characterization of Au Colloid Monolayers", *Anal. Chem.*, vol. 67, pp. 735-743 (1995).

Frens, *Nature Physical Science*, vol. 241, No. 105, pp. 20-22 (Jan. 1, 1973).

Ramsay, "DNA chips: State-of-the art", *Nat. Biotechnol.*, vol. 16, pp. 40-44 (1998).

Lander, "Array of Hope", *Nat. Genet.*, vol. 21(1), pp. 3-4 (1999).

Southern, et al, "Molecular interactions on microarrays", *Nat. Genet.*, vol. 21(1), pp. 5-9 (1999).

Duggan, et al, "Expression profiling using cDNA microarrays", *Nat. Genet.*, vol. 21(1), pp. 10 (1999).

Cheung, et al, "Making and reading microarrays", *Nat. Genet.*, vol. 21 (1), pp. 15-19 (1999).

Lipshutz, et al. "Hight density synthetic oligonucleotide arrays", *Nat. Genet.*, vol. 21(1), pp. 20-24 (1999).

Bowtell, "Options available-from start to finish-for obtaining expression data by microarray", *Nat. Genet.*, vol. 21(1), pp. 25-32 (1999).

Brown, et al, "Exploring the new world of the genome with DNA microarrays", *Nat. Genet.*, vol. 21(1), pp. 33-37 (1999).

Cole, et al, "The genetics of cancer—a 3D model", *Nat. Genet.*, vol. 21(1), pp. 38-41 (1999).

Hacia, "Resequencing and mutational analysis using oligonuclotide microarrays", *Nat. Genet.*, vol. 21(1), pp. 42-47 (1999).

Debouck, et al, "DNA microarrays in drug discovery and development", *Nat. Genet.*, vol. 21(1), pp. 48-50 (1999).

Bassett, et al, "Gene expression informatics—it's all in your time", *Nat. Genet.*, vol. 21(1), pp. 51-55 (1999).

Chakravarti, "Population genetics—making sense out of sequence", *Nat. Genet.*, vol. 21(1), pp. 56-60 (1999).

Rogers et al., "Immobilization of Oligonucleotides onto a Glass Support via Disulfide Bonds", *Anal. Biochem.*, vol. 266, pp. 23-30 (1999).

Highsmith et al., "Evaluation of CNBr, FMP and Hydrazide Resins for Immunoaffinity Purification of Factor IX", *Biotechniques*, vol. 12, No. 3, pp. 418-423 (1992).

Ghosh et al., "Covalent attachment of oligonucleotides to solid supports", *Nucleic Acids Research*, vol. 15, No. 13, pp. 5353-5372 (1987).

Kolchinsky et al., Analysis of SNPs and Other Genomic Variations Using Gel-Based Chips, Human Mutation, 2002, vol. 19, pp. 343-360, published online in Wiley InterScience (www.interscience.wiley.com).

Gill et al., "Degradation of Organophosphorous Nerve Agents by Enzyme-Polymer Nanocomposites: Efficient Biocatalytic Materials for Personal Protection and Large-Scale Detoxification", *Biotechnology and Bioengineering*, Nov. 20, 2000, pp. 400-410, vol. 70, No. 4, John Wiley & Sons.

Anspach et al., High-Performance Liquid Affinity Chromatography with Phenylboronic Acid, Benzamidine, Tri-L-alanine, and Concanavalin A Immobilized on 3-Isothiocyantopropyltriethoxysilane-Activated Nonporous Monodisperse Silicas, *Analytical Biochemistry*, vol. 179, pp. 171-181 (1989).

Huckel et al., Porous zirconia: a new support material for enzyme immobilization, *J. Biochem. Biophys. Methods*, vol. 31, pp. 165-179 (1996).

Wieser et al., "Plasma membrane glycoproteins covalently bound to silica beads as a model for molecular studies of cell-cell interactions in culture", *J. Biochem. Biophy. Methods*, vol. 15, pp. 13-22 (1987).

Highsmith F., et al., "Evaluation of CNBr, FMP and hydrazide resins for immunoaffinity purification of factor IX," *Biotechniques*, vol. 12, p. 418-426 (1992).

Kumar A., et al., "Silanized nucleic acids: a general platform for DNA immobilization," *Nucleic Acids Research*, vol. 28, p. 1-6 (2000).

Lindroos K., et al., "Minisequencing on oligonucleotide microarrays: comparison of immobilization chemistries," *Nucleic Acids Research*, vol. 29, No. 13, p. 1-7 (2001).

Ramsay G., "DNA chips: State-of-the art," *Nature Biotechnology*, vol. 16, p. 40-44 (1998).

Rogers Y., et al., "Immobilization of Oligonucleotides onto a Glass Support via Disulfide Bonds: A Method for Preparation of DNA Microarrays," *Analytical Biochemistry*, vol. 266, p. 23-30 (1999).

Weetall H., "Preparation of Immobilized Proteins Covalently Coupled Through Silane Coupling Agents to Inorganic Supports," *Applied Biochemistry and Biotechnology*, vol. 41, p. 157-188 (1993).

Beyer, et al., "Surface Modification via Reactive Polymer Interlayers", *Langmuir* 1996, vol. 12, p. 2514-2518.

Walsh et al., "Optimizing the immobilization of single-stranded DNA onto glass beads", *J. Biochem. Biophys. Methods* 47, p. 221-231 (2001).

Sompuram et al., "A Novel Quality Control Slide for Quantitative Immunohistochemistry Testing", *Journal of Histochemistry and Cytochemistry*, vol. 50, p. 1425-1433 (2002).

Sompuram et al., "Synthetic Peptides Identified from Phage-displayed Combinatorial Libraries as Immunodiagnostic Assay Surrogate Quality-Control Targets", *Clinical Chemistry* vol. 48:3, p. 410-420 (2002).

Sompuram et al., "A Novel Microscope Slide Adhesive for Poorly Adherent Tissue Sections", *Journal of Histotechnology*, vol. 26, No. 2, p. 117-123 (2003).

Sompuram et al., "A water-stable protected isocyanate glass array substrate", *Anal. Biochem.*, vol. 326, p. 55-68 (2004).

Material Safety Data Sheet for Aliphatic Isocyanate, http://msds.ogden.disa.mil/msds/owa/web_msds.display?imsdsnr=188672, 2005.

Parker, Anthony A., "A Technical Review of Organosilanes and Adhesion", http://aaparkerconsulting.home.att.net/, 2001.

Pierce Biotechnology, Instructions for EDC, http://www.piercenet.com, May 2002.

Spanne, Márten, "Derivatization and Analysis of Aromatic Iscyanates with Dibutylamine and Liquid Chromatography", Lund Institute of Technology, Lund University, Publication 47, ISSN 1104-1080, 1998.

Weetall, H. H., "Covalent Coupling Methods for Inorganic Support Materials", *Methods in Enzymology*, 1976, vol. 44, pp. 134-139.

Sompuram et al., "A water-stable protected isocyanate glass array substrate", Anal. Biochem., vol. 326, pp. 55-68 (2004).

Dickinson, et al, "A Novel Probe for Free Radicals featuring Expoxide Cleavage", *J. Chem. Soc.*, pp. 1179-1184, (1990).

Satchell, et al, "Acylation by Ketens and Isocyanates. A Mechanistic Comparison", *Chem. Soc. Rev.*, pp. 231-250, (1975).

Lenhart, et al, "Immobilizing a Fluorscent Dye Offers Potential to Investigate the Glass/Resin Interface", *Journal of Colloid and Interface Science*, vol. 221, pp. 75-86, (2000).

WATER

DMF

WATER

THE ONLY TIME "BRANCHING" WAS SEEN WITH THE DMF BUFFER WAS THE CASE ABOVE WHERE IT SEEMS THAT THE AREA AROUND THE SPOTS IS OVERHYDRATED.

SILYL
BLANK
BLANK
SILYL
SILYL
SILYL
SILYL
BLANK

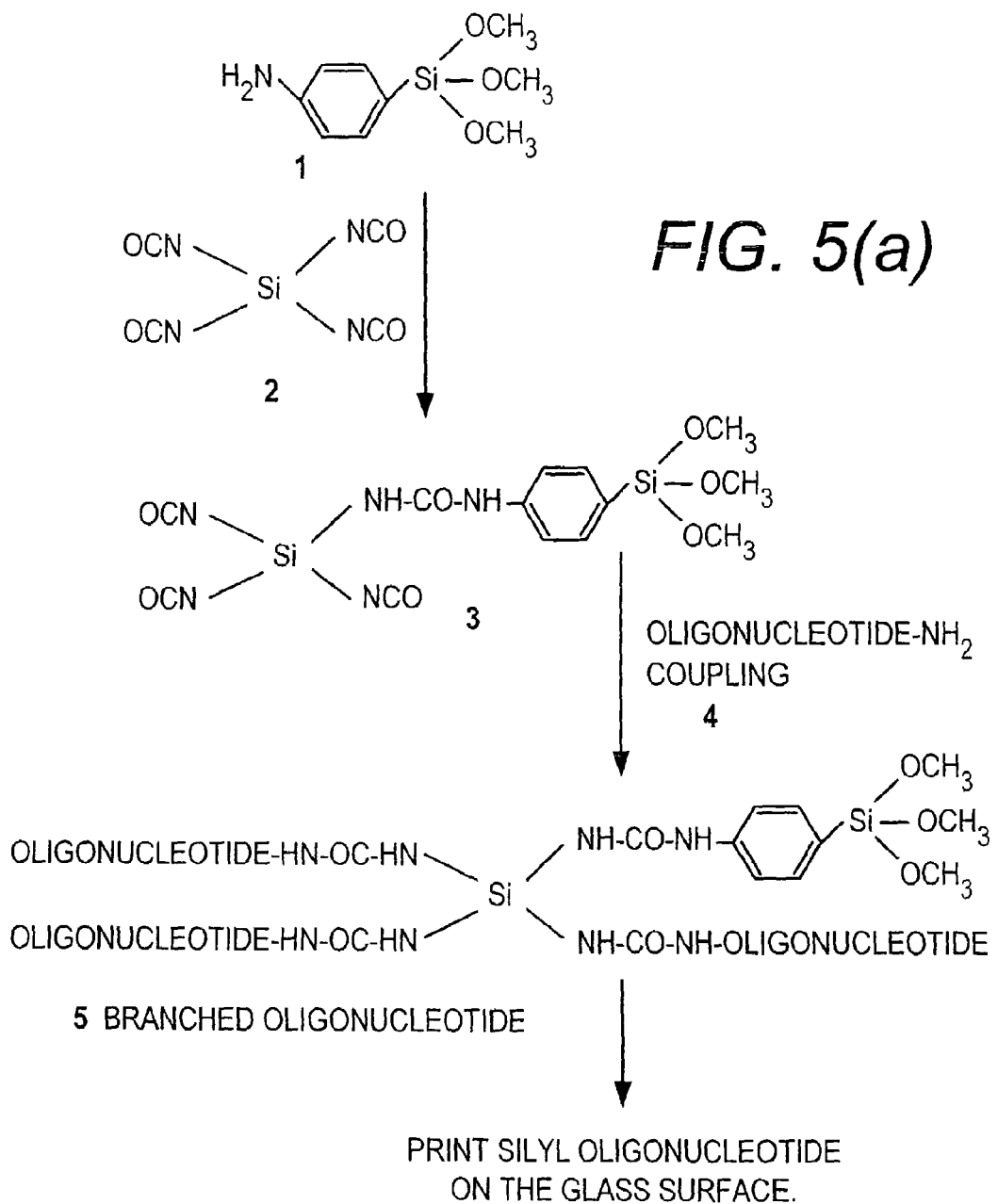

PRINT SILYL OLIGONUCLEOTIDE
ON THE GLASS SURFACE.

PLATE NOS. 1 (FIRST PLATE), 2 (MIDDLE PLATE), AND 3 (LAST PLATE)

METHOD FOR ATTACHMENT OF SILYLATED MOLECULES TO GLASS SURFACES

CROSS-REFERENCE

This application is a divisional of U.S. application Ser. No. 10/447,073, filed May 28, 2003, which claims the benefit of U.S. Provisional application No. 60/383,564, filed May 28, 2002, which are incorporated by reference in their entirety.

BACKGROUND OF THE INVENTION

Surface modification plays an important role in microarray biomolecule detection technology for controlling backgrounds and spot morphology. Several modifications were developed using different type of commercially available silanes such as silyl amines, aldehydes, thiols etc. for immobilization of biomolecules such as oligonucleotides. After coating the surface with reactive silanes, the next challenge is immobilization of required biomolecules on the modified surface. The surface loadings always vary with different silanes and even same silane may not give reproducible results. Reproducibility of optimum surface loading has always been a great challenge in this field since surface loading dictates the performance of the assay. Even with simple linear molecules for immobilization, the optimum loading on the surface is difficult to achieve.

Attaching DNA to a modified glass surface is a central step for many applications in DNA diagnostics industry including gene expression analysis. In general, DNA can be attached to a glass surface either through non-covalent, ionic interactions, or through multi-step processes or simple coupling reactions. Several methods have been reported in the literature using glass surface modified with different types of silylating agents[1-6]. All these reported methods involve silylating step which uses expensive reagents and analytical tools. Also, these methods are also multi-step processes that are labor intensive and expensive[8-9]. Earlier reported methods have involved a laborious synthesis and time consuming procedure[7]. Indeed, many of the current immobilization methods suffer from one or more of a number of disadvantages. Some of these are, complex and expensive reaction schemes with low oligonucleotide loading yields, reactive unstable intermediates prone to side reactions and unfavorable hybridization kinetics of the immobilized oligonucleotide. The efficient immobilization of oligonucleotides or other molecules on glass surface in arrays requires a) simple reliable reactions giving reproducible loading for different batches, b) stable reaction intermediates, c) arrays with high loading and fast hybridization rates, d) high temperature stability, e) low cost, f) specific attachment at either the 5'- or 3'-end or at an internal nucleotide and g) low background.

The present invention represents a significant step in the direction of meeting or approaching several of these objectives.

SUMMARY OF THE INVENTION

The present invention fulfills the need in the art for methods for the attachment of molecules such as oligonucleotides onto unmodified surfaces such as a glass surface without the need for laborious synthetic steps, with increase surface loading densities, and with greater reproducibility and which avoids the need for pre-surface modifications. Molecules such as DNA can be silylated at either the 3' or 5' ends as discussed below and the 3' or 5'-silylated DNA may then be covalently attached directly to a surface such as a pre-cleaned glass surface (Scheme) for use in hybridization assays. Furthermore, thorough the use of certain silylating reagents, it is now possible to further enhance surface loading densities by using modified silylating agents having multiple molecules attached thereto. The present invention thus provides novel methods for attaching molecules onto a substrate, devices prepared by such methods, and compositions. This method provides great advantages over the present technology in terms of simplicity, cost, speed, safety, and reproducibility.

Thus, in one embodiment of the invention, a method is provided for immobilizing a molecule onto a surface, said method comprising the steps of:

(a) contacting the molecule with an agent so as to form a reactive intermediate, said agent having a formula i:

$$(R_1)(R_2)(R_3)Si-X-NCY \qquad \text{i}$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; and Y represents oxygen or sulfur, with the proviso that at least one of $R_1$, $R_2$ or $R_3$ represents $C_1$-$C_6$ alkoxy; and (b) contacting the reactive intermediate with said surface so as to immobilize the molecule onto said surface.

In one aspect of this embodiment, a method is provided for immobilizing a molecule onto a glass surface.

In another embodiment of the invention, a method is provided for immobilizing a molecule onto a surface, said method comprising the steps of:

(a) contacting $Si(NCY)_4$ wherein Y represents oxygen or sulfur with an agent so as to form a first reactive intermediate, said agent having a formula ii:

$$(R_1)(R_2)(R_3)Si-X-Z \qquad \text{ii}$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; and Z represents a hydroxy or amino group, with the proviso that at least one of $R_1$, $R_2$ or $R_3$ represents $C_1$-$C_6$ alkoxy;

(b) contacting the first reactive intermediate with a molecule so as to form a second reactive intermediate;

(c) contacting the second reactive intermediate with said surface so as to immobilized the molecule onto said surface. The method allows for the production of branched captured molecules structures such as branched oligonucleotides on a surface which is useful for enhancing detection of target analytes such as nucleic acids.

In one aspect of this embodiment of the invention, a method is provided for immobilizing a molecule onto a glass surface.

In another embodiment of the invention, a compound is provided having the formula iii:

$$(R_1)(R_2)(R_3)Si-X-NHCYL-M \qquad \text{iii}$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; L represents a linking group; and M represents a molecule, with the proviso that at least one of $R_1$, $R_2$, or $R_3$ represent $C_1$-$C_6$ alkoxy.

In another embodiment of the invention, a compound is provided having a formula iv:

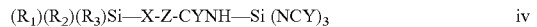
(R₁)(R₂)(R₃)Si—X-Z-CYNH—Si (NCY)₃      iv wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy.

In another embodiment of the invention, a compound is provided having a formula v:

(R₁)(R₂)(R₃)Si—X-Z-CYNH—Si(NHCYL-M)₃      v wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; L represents a linking group; and Z represents oxygen or NH; and M represents a molecule, with the proviso that at least one of $R_1$, $R_2$, or $R_3$ represent $C_1$-$C_6$ alkoxy.

In another embodiment of the invention, a compound is provided having a formula vi:

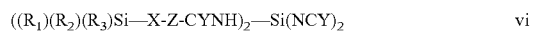
((R₁)(R₂)(R₃)Si—X-Z-CYNH)₂—Si(NCY)₂      vi wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy.

In another embodiment of the invention, a compound is provided having a formula vii:

((R₁)(R₂)(R₃)Si—X-Z-CYNH)₂Si(NHCYL-M)₂      vii wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; L represents a linking group; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH; and M represents a molecule, with the proviso that at least one of $R_1$, $R_2$, or $R_3$ represents $C_1$-$C_6$ alkoxy.

In another embodiment of the invention, kits are provided for preparing modified substrates. The kits may include reagents for silyating molecules and optional substrates.

These and other embodiments of the invention will become apparent in light of the detailed description below.

DESCRIPTION OF THE INVENTION

Figure 1:
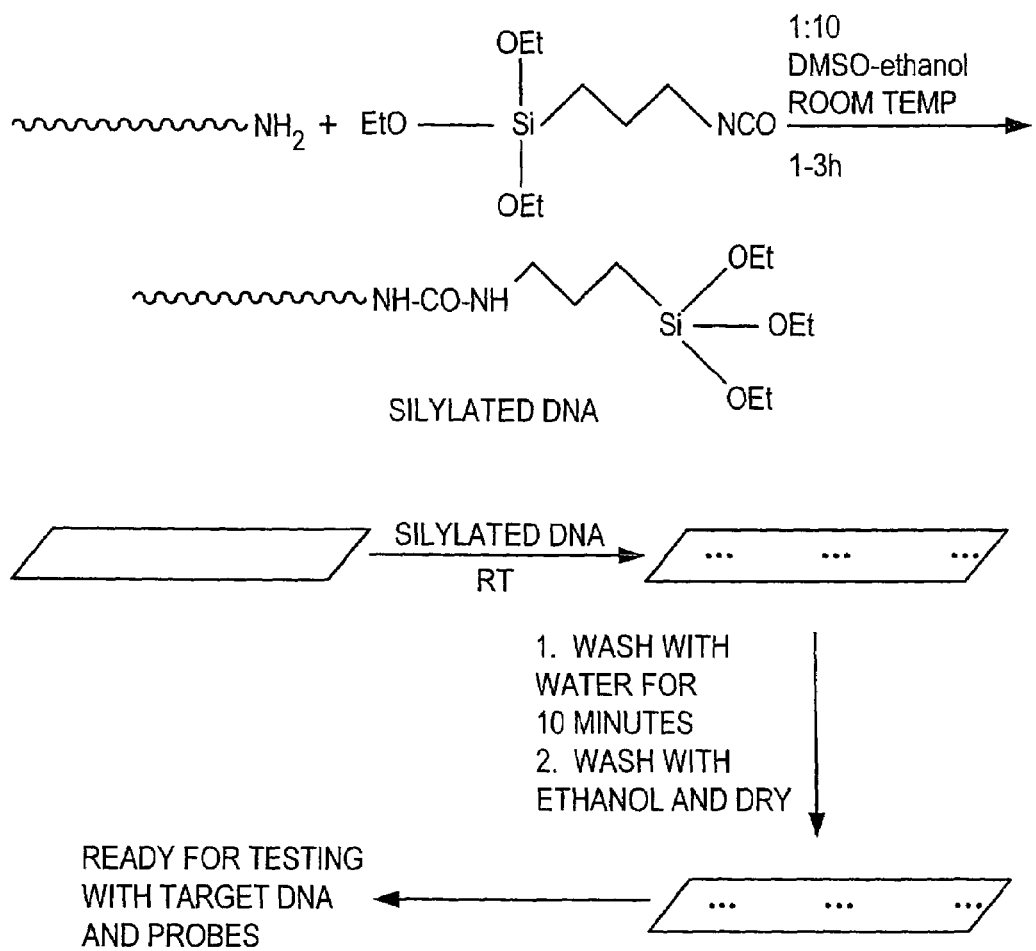
FIG. 1 is a scheme that illustrates one embodiment of the invention. The scheme shows the modification of a molecule such as an oligonucleotide modified at either a 3'-amino or 5'-amino to produce a silylated DNA intermediate. This silylated intermediate is then spotted onto a surface of a substrate, e.g., glass substrate and washed.

All patents, patent applications, and references cited herein are incorporated by reference in their entirety.

As defined herein, the term "molecule" refers to any desired specific binding member that may be immobilized onto the surface of the substrate. The "specific binding member," as defined herein, means either member of a cognate binding pair. A "cognate binding pair," as defined herein, is any ligand-receptor combination that will specifically bind to one another, generally through non-covalent interactions such as ionic attractions, hydrogen bonding, Vanderwaals forces, hydrophobic interactions and the like. Exemplary cognate pairs and interactions are well known in the art and include, by way of example and not limitation: immunological interactions between an antibody or Fab fragment and its antigen, hapten or epitope; biochemical interactions between a protein (e.g. hormone or enzyme) and its receptor (for example, avidin or streptavidin and biotin), or between a carbohydrate and a lectin; chemical interactions, such as between a metal and a chelating agent; and nucleic acid base pairing between complementary nucleic acid strands; a peptide nucleic acid analog which forms a cognate binding pair with nucleic acids or other PNAs. Thus, a molecule may be a specific binding member selected from the group consisting of antigen and antibody-specific binding pairs, biotin and avidin binding pairs, carbohydrate and lectin bind pairs, complementary nucleotide sequences, complementary peptide sequences, effector and receptor molecules, enzyme cofactor and enzymes, and enzyme inhibitors and enzymes. Other specific binding members include, without limitation, DNA, RNA, polypeptide, antibody, antigen, carbohydrate, protein, peptide, amino acid, carbohydrate, hormone, steroid, vitamin, drug, virus, polysaccharides, lipids, lipopolysaccharides, glycoproteins, lipoproteins, nucleoproteins, oligonucleotides, antibodies, immunoglobulins, albumin, hemoglobin, coagulation factors, peptide and protein hormones, non-peptide hormones, interleukins, interferons, cytokines, peptides comprising a tumor-specific epitope, cells, cell-surface molecules, microorganisms, fragments, portions, components or products of microorganisms, small organic molecules, nucleic acids and oligonucleotides, metabolites of or antibodies to any of the above substances. Nucleic acids and oligonucleotides comprise genes, viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids. Preparation of antibody and oligonucleotide specific binding members is well known in the art. The molecules (M) have at least one or more nucleophilic groups, e.g., amino, carboxylate, or hydroxyl, that are capable of linking or reacting with the silylating agents to form a reactive silylated molecule which is useful for modifying the surfaces of substrates. These nucleophilic groups are either already on the molecules or are introduced by known chemical procedures.

As defined herein, the term "substrate" refers any solid support suitable for immobilizing oligonucleotides and other molecules are known in the art. These include nylon, nitrocelluose, activated agarose, diazotized cellulose, latex particles, plastic, polystyrene, glass and polymer coated surfaces. These solid supports are used in many formats such as membranes, microtiter plates, beads, probes, dipsticks, optical fibers, etc. Of particular interest as background to the present invention is the use of glass and nylon surfaces in the preparation of DNA microarrays which have been described in recent years (Ramsay, Nat. Biotechnol., 16: 40-4 (1998)). The journal Nature Genetics has published a special supplement describing the utility and limitations of microarrays (Nat. Genet., 21(1): 1-60 (1999)). Typically the use of any solid support requires the presence of a nucleophilic group to react with the silylated molecules of the invention that contain a "reactive group" capable of reacting with the nucleophilic group. Suitable nucleophilic groups or moieties include hydroxyl, sulfhydryl, and amino groups or any moiety that is capable of coupling with the silyated molecules of the invention. Chemical procedures to introduce the nucleophilic or the reactive groups onto solid support are known in the art, they include procedures to activate nylon (U.S. Pat. No. 5,514, 785), glass (Rodgers et al., Anal. Biochem., 23-30 (1999)), agarose (Highsmith et al., J., Biotechniques 12: 418-23 (1992) and polystyrene (Gosh et al., Nuc. Acid Res., 15: 5353-5372 (1987)). The preferred substrate is glass.

The term "analyte," or "target analyte", as used herein, is the substance to be quantitated or detected in the test sample using devices prepared by the method of the present invention. The analyte can be any substance for which there exists a naturally occurring specific binding member (e.g., an antibody, polypeptide, DNA, RNA, cell, virus, etc.) or for which a specific binding member can be prepared, and the analyte can bind to one or more specific binding members in an assay.

In one embodiment of the invention, a method is provided for immobilizing a molecule onto a substrate surface, said method comprising the steps of contacting the molecule with an agent so as to form a reactive intermediate, said agent having a formula i:

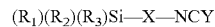

$(R_1)(R_2)(R_3)Si—X—NCY$          i wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; and Y represents oxygen or sulfur, with the proviso that at least one of $R_1$, $R_2$ or $R_3$ represents $C_1$-$C_6$ alkoxy; and contacting the reactive intermediate with said surface so as to immobilized the molecule onto said surface.

In practice, the molecule is contacted with the agent in solution. Generally, the molecule is dissolved in a solution and agent is added drop-wise to the molecule solution. Suitable, but non-limiting, examples of solvents used in preparing the solution include DMF, DMSO, ethanol and solvent mixtures such as DMSO/ethanol. The preferred solvent is ethanol. Water is preferably excluded from the reaction solvent because water may interfere with the efficient modification of the molecule. However, if water is necessary to increase solubility of the molecule in the solution, the amount of water generally ranges from about 0.1% to about 1%, usually no greater than 1%.

The amount of molecule to agent generally ranges from about 1 to about 1.5 typically from about 1 to about 1.1, preferably from about 1 to about 1 molar equivalents. The reaction may be performed in any suitable temperature. Generally, the temperature ranges between about 0° C. and about 40° C., preferably from about 20° C. to about 25° C. The reaction is stirred for a period of time until sufficient amount of molecule and agent reacts to form a reactive intermediate. The reactive intermediate has a structure defined by formula iii.

Thereafter, the reaction solution containing the reactive intermediate is then concentrated and dissolved in desired solvent to provide a spotting solution which is then applied to the surface of a substrate. The reactive intermediate is applied as a spotting solution. Any suitable solvent may be used to prepare the spotting solution. Suitable, but non-limiting, examples of solvents used in preparing the spotting solution include DMF, DMSO, and ethanol as well as any suitable solvent mixtures such as DMF/pyridine. Any suitable concentration of the spotting solution may be prepared, generally the concentration of the spotting solution is about 1 mM. Any suitable spotting technique may be used to produce spots. Representative techniques include, without limitation, manual spotting, ink-jet technology such as the ones described in U.S. Pat. Nos. 5,233,369 and 5,486,855; array pins or capillary tubes such as the ones described in U.S. Pat. Nos. 5,567,294 and 5,527,673; microspotting robots (e.g., available from Cartesian); chipmaker micro-spotting device (e.g., as available from TeleChem Interational). Suitable spotting equipment and protocols are commercially available such as the ArrayIt® chipmaker 3 spotting device. The spotting technique can be used to produce single spots or a plurality of spots in any suitable discrete pattern or array.

In the preferred embodiment, the agent is triethoxysilylisocyanate. The preferred molecule is a nucleic acid.

In another embodiment of the invention, a method is provided for immobilizing a molecule onto a substrate surface, said method comprising the steps of contacting $Si(NCY)_4$ with an agent so as to form a first reactive intermediate, said agent having a formula ii:

$$(R_1)(R_2)(R_3)Si-X-Z \qquad \qquad ii$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; wherein Y represents oxygen or sulfur; and Z represents a hydroxy or amino group, with the proviso that at least one of $R_1$, $R_2$ or $R_3$ represents $C_1$-$C_6$ alkoxy; contacting the first reactive intermediate with a molecule so as to form a second reactive intermediate; and contacting the second reactive intermediate with said surface so as to immobilized the molecule onto said surface.

In this embodiment of the invention, the method provide for a modification of substrate surfaces with branched molecules so as to increase molecule loading on the substrate surface. These branched molecules behave like dendrimers to enhance sensitivity in assay performance. In practice, either $Si(NCO)_4$ or $Si(NCS)_4$ are reacted with a compound of formula ii to form a first reactive intermediate having the formula iv:

$$(R_1)(R_2)(R_3)Si-X-Z-CYNH-Si(NCY)_3 \qquad \qquad iv$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy.

Generally, $Si(NCO)_4$ or $Si(NCS)_4$ is dissolved in a suitable dry solvent as described above. In practice, ethanol is the preferred solvent. The resulting ethanol solution is contained in a reaction flask and a solution of formula ii compound is added to the reaction flask. The formula ii solution may include any of the dried solvents described above. In practice, ethanol is the preferred solvent. The reaction temperature generally ranges from about 0° C. to about 40° C., preferably about 22° C. The reaction mixture is allowed to stir from about 1 min to about 60 min, usually about 5 min to about 10 min, until it reaches completion. The molar amount of $Si(NCO)_4$ or $Si(NCS)_4$ to formula ii compound generally ranges from about 3:1 to 1:1, preferably about 1:1.

Thereafter, the molecule is contacted with the first reactive intermediate to form a second reactive intermediate having the formula v:

$$(R_1)(R_2)(R_3)Si-X-Z-CYNH-Si(NHCYL-M)_3 \qquad \qquad v$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; L represents a linking group; Y represents oxygen or sulfur; and Z represents oxygen or NH; and M represents a molecule, with the proviso that at least one of $R_1$, $R_2$, or $R_3$ represent $C_1$-$C_6$ alkoxy. The linking group L may be a nucleophile that is naturally present or chemically added to the molecule such as an amino, sulfhydryl group, hydroxy group, carboxylate group, or any suitable moiety. L may represent —NH, —S—, —O—, or —OOC—.

The molecule is contacted with the first reactive intermediate in solution. Generally, the molecule is dissolved in a solvent and added dropwise to the reaction flask containing the first reactive intermediate. The molecule is generally mixed in any suitable solvent as described above. The molar amount of molecule to first reactive intermediate generally ranges from about 1 to about 10 typically from about 1 to about 3, preferably from about 1 to about 4. The reaction may be performed in any suitable temperature. Generally, the temperature ranges between about 0° C. and about 40° C., preferably from about 20° C. to about 25° C. The reaction is stirred for a period of time until sufficient amount of molecule and first reactive intermediate reacts to form a second reactive intermediate. Generally, an excess amount of molecule is used to react with the first reactive intermediate. In practice, typically at least 3 equivalents of molecule to 1 equivalent of first reactive intermediate is used.

Thereafter, the second reactive intermediate is then applied to the surface of a substrate using techniques described above.

In another aspect of this invention, if the ratio of Si(NCO)$_4$ or Si(NCS)$_4$ to formula ii compound is about 1:2 equiv./equiv., a first reactive intermediate is formed having the formula vi:

$$((R_1)(R_2)(R_3)Si-X-Z-CYNH)_2-Si(NCY)_2 \qquad vi$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy. Preferably, $R_1$, $R_2$ and $R_3$ represent methoxy, X represents phenyl, Y represents oxygen, and Z represents NH.

Thereafter, the molecule is contacted with the first reactive intermediate of formula vi as described above to produce a second reactive intermediate having the formula vii:

$$((R_1)(R_2)(R_3)Si-X-Z-CYNH)_2Si(NHCYL-M)_2 \qquad vii$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; L represents a linking group; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH; and M represents a molecule, with the proviso that at least one of $R_1$, $R_2$, or $R_3$ represent $C_1$-$C_6$ alkoxy. The linking group L may be a nucleophile that is naturally present or chemically added to the molecule such as an amino, sulfhydryl group, hydroxy group, carboxylate group, or any suitable moiety. L may represent —NH, —S—, —O—, or —OOC—. Generally, an excess amount of molecule is used to react with the first reactive intermediate. In practice, typically at least 3 equivalents of molecule to 1 equivalent of first reactive intermediate is used.

Thereafter, the second reactive intermediate is then applied to the surface of a substrate using the techniques described above.

In another embodiment of the invention, a compound is provided having the formula iii:

$$(R_1)(R_2)(R_3)Si-X-NHCYL-M \qquad iii$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; L represents a linking group; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and M represents a molecule, with the proviso that at least one of $R_1$, $R_2$, or $R_3$ represent $C_1$-$C_6$ alkoxy. The linking group L may be a nucleophile that is naturally present or chemically added to the molecule such as an amino, sulfhydryl group, hydroxy group, carboxylate group, or any suitable moiety. L may represent —NH, —S—, —O—, or —OOC—. In the preferred embodiment, $R_1$, $R_2$, and $R_3$ represent alkoxy, L represents —NH—, X represents propyl, and Y represents O. The compound is useful for modifying substrate surfaces with a desired molecule.

In another embodiment of the invention, a compound is provided having a formula iv:

$$(R_1)(R_2)(R_3)Si-X-Z-CYNH-Si(NCY)_3 \qquad iv$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy. In the preferred embodiment, $R_1$, $R_2$, and $R_3$ represent ethoxy or methoxy, X represents benzyl, Y represents oxygen, and Z represents NH. The compound is useful for modifying molecules so that they can be attached to substrate surfaces.

In another embodiment of the invention, a compound is provided having a formula v:

$$(R_1)(R_2)(R_3)Si-X-Z-CYNH-Si(NHCYL-M)_3 \qquad v$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; L represents a linking group; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH; and M represents a molecule, with the proviso that at least one of $R_1$, $R_2$, or $R_3$ represent $C_1$-$C_6$ alkoxy. The linking group L may be a nucleophile that is naturally present or chemically added to the molecule such as an amino, sulfhydryl group, hydroxy group, carboxylate group, or any suitable moiety. L may represent —NH, —S—, —O—, or —OOC—. In the preferred embodiment, $R_1$, $R_2$, and $R_3$ represent methoxy or ethoxy, X represents 3- or 4-phenyl, Y represents oxygen, and Z represents NH. The compound is useful for modifying molecules so that they can be attached to substrate surfaces.

In another embodiment of the invention, a device is provided for the detection of target analytes in a sample. The device comprises a surface having an immobilized molecule as a specific binding member to the target analyte, wherein said surface is prepared by any of the above methods. The preferred surface is a glass surface. The surface may have one or more different specific binding members attached thereto in an array to allow for the detection of different portions of a target analyte or multiple different types of target analytes.

In another embodiment of the invention, a kit is provided. The kit may comprise one or more containers containing any of the silylating agents mentioned above with an optional substrate, and a set of instructions.

EXAMPLES

The invention is demonstrated further by the following illustrative examples. The examples are offered by way of illustration and are not intended to limit the invention in any manner. In these examples all percentages are by weight if for solids and by volume if for liquids, and all temperatures are in degrees Celsius unless otherwise noted.

Example 1

Preparation of DNA Array Chips

This Example provides a general procedure for the covalent attachment of a molecule, e.g., 3' or 5'-silylated DNA, directly to surfaces such as pre-cleaned glass surface via single silylated molecule or dendritic silylated molecule procedure.

(a) Method No. 1

As shown in FIG. 1, a method is shown for attaching a 3'-amino or 5'-amino DNA molecule to a pre-cleaned glass surface. 3'-Amine linked DNA is synthesized by following standard protocol for DNA synthesis on DNA synthesizer. The 3' amine modified DNA synthesized on the solid support was attached through succinyl linker to the solid support. After synthesis, DNA attached to the solid support was released by using aqueous ammonia, resulting in the generation of a DNA strand containing a free amine at the 3'-end. The crude material was purified on HPLC, using triethyl ammonium acetate (TEAA) buffer and acetonitrile. The dimethoxytrityl (DMT) group was removed on the column itself using triflouroacetic acid.

After purification, 1 equivalents of 3'-amine linked DNA was subsequently treated with 1.2 equivalents of triethoxysilyl isocyanate (GELEST, Morrisville, Pa., USA) for 1-3 h in 10% DMSO in ethanol at room temperature. Traces of water that remained in the DNA following evaporation did not effect the reaction. After 3 h, the reaction mixture was evaporated to dryness and spotted directly on pre-cleaned glass surface using an arrayer (Affymetrix, GMS 417 arrayer with 500 micron pins for spotting). Typically, 1 mM silylated DNA was used to array a glass surface and the arrayed substrate is then kept in the chamber for 4 h-5 h. Thereafter, the slides were incubated in nanopure water for 10 minutes to remove the unbound DNA, washed with ethanol, and dried in the dessicator. After drying, these plates were tested with target DNA samples.

Figure 2:
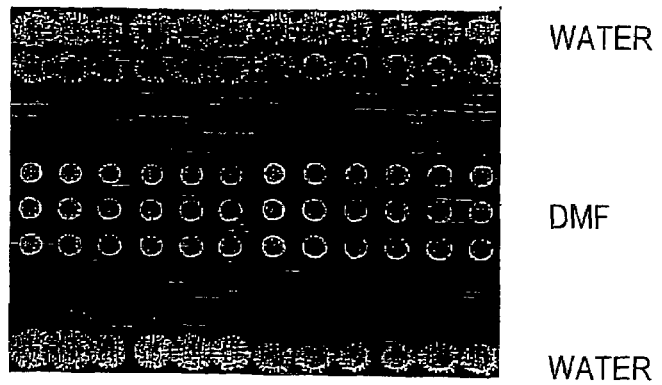
FIG. 2 illustrates spot morphology after spotting a substrate with a DMF solution containing a silylated DNA in water or DMF. Branching and spreading of the spot was observed with the aqueous solution.
Figure 3:
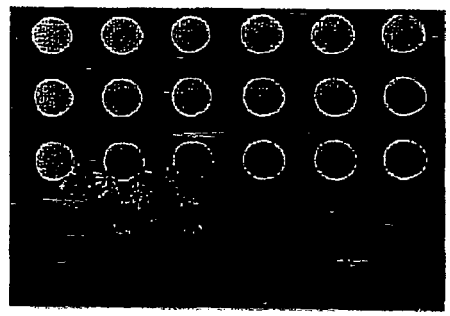
FIG. 3 illustrates spot morphology using a DMF solution containing a silyated DNA spotted on a overhydrated substrate. Branching of the spot was observed with the over hydrated substrate.
Figure 4:
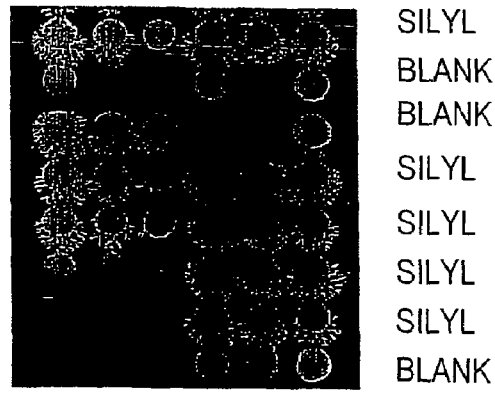
FIG. 4 illustrates spot morphology with an aqueous solution containing no silylated DNA (blank control) and with silylated DNA (silyl).

In a preliminary study using linear silyl oligonucleotides prepared by the above procedure to spot a glass surface, it was observed that spotting in DMSO or DMF medisurprisingly controlled spot branching or diffusion. See FIG. 2. The spot morphology was clean and discrete. If the substrate was overhydrated in the dessicator chamber prepared by filing a portion of a chamber with water and storing the glass slides on a rack above the water level overnight, the slides become overhydrated. Undesirable branching of the spot was observed on overhydrated slides, even when DMSO or DMF solvent is used. See FIG. 3. When water was used as the sole solvent for spotting, the resultant spots were branched out and spread to other spots. See FIG. 4. Without being bound to any theory of operation, an aqueous spotting solution and/or the presence of water in a overhydrated substrate results in the polymerization of silyl oligonucleotides and thus interfered with the modification of the surface with the desired molecule. Thus, dried polar aprotic solvents such as DMF, DMSO and dried polar solvents like ethanol, isopropanol and mixture of solvents like DMF/Pyridine were found to be suitable solvents for arraying the silyl modified oligonucleotides. The presence of water (>1%) in the spotting solution or over hydration of slidesresults in spot branching after arraying. Spot branching is undesirable because it may lead to false positive results in binding studies.

(b) Method No. 2

Figure 5B:
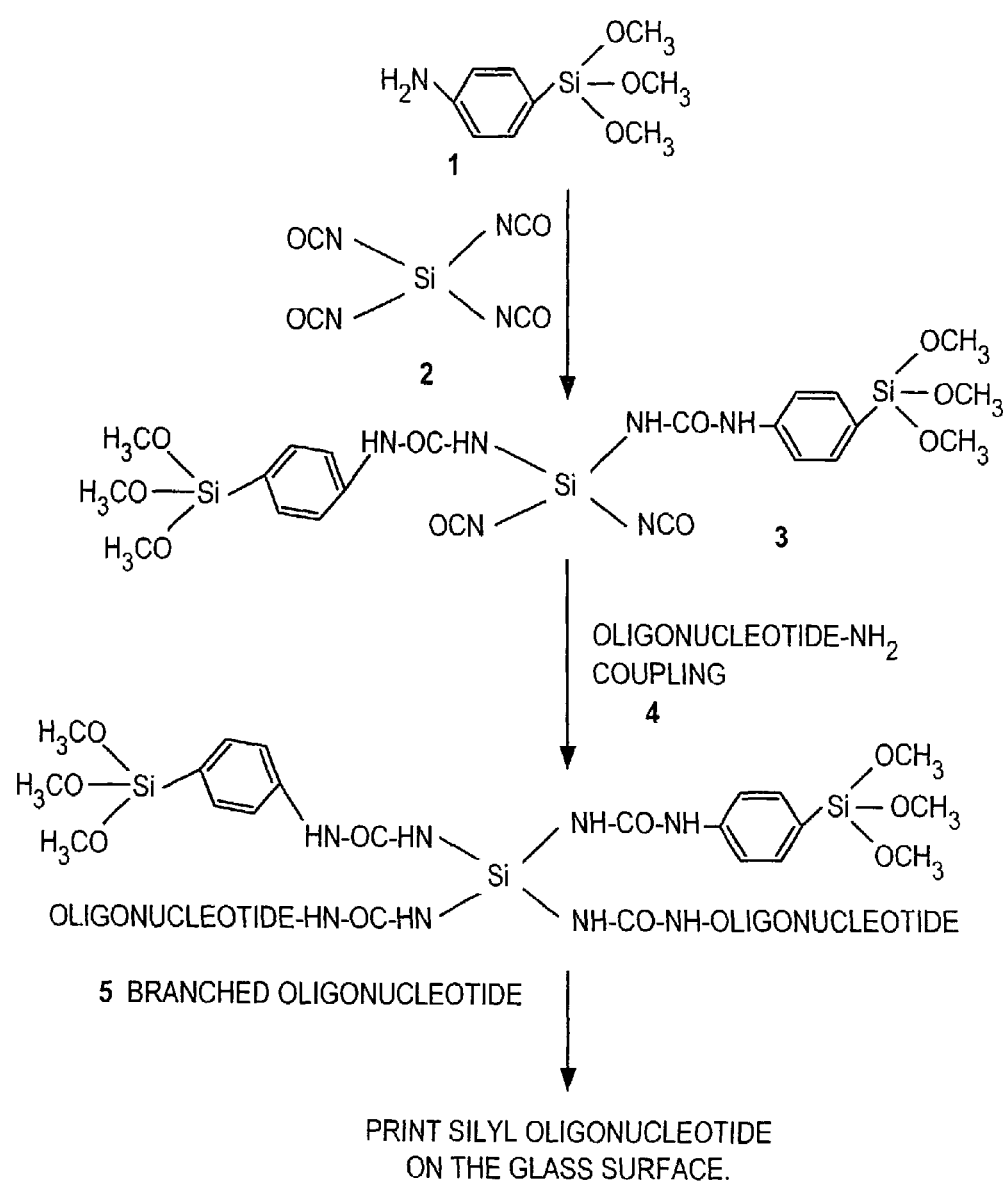
FIG. 5 is (a) a scheme that illustrates another embodiment of the invention. The scheme shows the coupling of a tetraisocyanatosilane with a 1-amino-4-triethoxysilylbenzene to form a first reactive intermediate 4. The reactive intermediate is then coupled to a oligonucleotide having a free 3' or 5'-amino group to silylated DNA intermediate as a second reactive intermediate containing three molecules bound thereto. This silylated intermediate is then spotted onto a surface of a substrate, e.g., glass substrate. In part (b), a scheme is provided that illustrates another embodiment of the invention. The scheme shows the coupling of a tetraisocyanatosilane with a 1-amino-4-triethoxysilylbenzene to form a first reactive intermediate 4. The reactive intermediate is then coupled to a oligonucleotide having a free 3' or 5'-amino group to silylated DNA intermediate as a second reactive intermediate containing two molecules bound thereto.

As shown in FIG. 5, a method is shown for attaching multiple 5' or 3' amino DNA molecules to a glass surface. To 1 equivalent of silyl amine in dry acetonitrile, 1.2 equivalents of tetraisocyante is added dropwise and the reaction mixture is stirred at room temperature for 10 minutes to form compound 3. 5' or 3'-amine linked oligonucleotide is synthesized and deprotected using aqueous ammonia conditions by conventional procedures. After HPLC purification, 5' or 3'-amine free oligonucleotide is treated with compound 3 in a 1:10 DMSO/ethanol (v/v) mixture. After 10 minutes, the modified oligonucleotides are evaporated under vacuum and spotted on unmodified glass surface in DMSO or DMF media.

Example 2

Detection of Factor V Target Sequence Using a DNA Array Chip

This Example illustrates that DNA plates prepared as described in Example 1 are useful for sandwich hybridization assays for detection of nucleic acid targets.

(a) Gold Colloid Preparation:

Gold colloids (13 nm diameter) were prepared by reduction of $HAuCl_4$ with citrate as described in Frens, *Nature Phys. Sci.*, 241, 20 (1973) and Grabar, *Anal. Chem.*, 67, 735 (1995). Briefly, all glassware was cleaned in aqua regia (3 parts HCl, 1 part $HNO_3$), rinsed with Nanopure $H_2O$, then oven dried prior to use. $HAuCl_4$ and sodium citrate were purchased from Aldrich Chemical Company. Aqueous $HAuCl_4$ (1 mM, 500 mL) was brought to reflux while stirring. Then, 38.8 mM sodium citrate (50 mL) was added quickly. The solution color changed from pale yellow to burgundy, and refluxing was continued for 15 min. After cooling to room temperature, the red solution was filtered through a Micron Separations Inc. 1 micron filter. Au colloids were characterized by UV-Vis spectroscopy using a Hewlett Packard 8452A diode array spectrophotometer and by Transmission Electron Microscopy (TEM) using a Hitachi 8100 transmission electron microscope. Gold particles with diameters of 13 nm will produce a visible color change when aggregated with target and probe oligonucleotide sequences in the 10-35 nucleotide range.

(b) Synthesis of Oligonucleotides:

Oligonucleotides were synthesized on a 1 micromole scale using a Milligene Expedite DNA synthesizer in single column mode using phosphoramidite chemistry. Eckstein, F. (ed.) *Oligonucleotides and Analogues: A Practical Approach* (IRL Press, Oxford, 1991). All solutions were purchased from Milligene (DNA synthesis grade). Average coupling efficiency varied from 98 to 99.8%, and the final dimethoxytrityl (DMT) protecting group was cleaved from the oligonucleotides to do final epiendrosterone coupling on the synthesizer itself. Capture strands were synthesized with DMT on procedure and purified on HPLC system.

(c) Purification of Oligonucleotides

Reverse phase HPLC was performed with using Agilent 1100 series system equipped with Tosch Biosep Amberchrom MD-G CG-300S column (10×118 mm, 35 μm particle size) using 0.03 M $Et_3NH^+OAc^-$ buffer (TEAA), pH 7, with a 1%/min. gradient of 95% $CH_3CN/5%$ TEAA. The flow rate was 1 mL/min. with UV detection at 260 nm. The final DMT attached was deprotected on HPLC column itself using 1-3% trifluoro acetic acid and TEAA buffer. After collection and evaporation of the buffer contained the DMT cleaved oligonucleotides, was then evaporated to near dryness. The amount of oligonucleotide was determined by absorbance at 260 nm, and final purity assessed by reverse phase HPLC.

The same protocol was used for epiendrosterone linked-oligonucleotides for probe preparation and no DMT removal needed[10].

(d) Attachment of Oligonucleotides to Gold Nanoparticles

Probes used in the Example: (3'-act tta aca ata g-$a_{20}$-Epi-5' and 3'-t taa cac tcg c-a20-Epi-5') (SEQ ID NO:1) was attached in the following fashion. These probes were designed for M13 target sequence detection.

A 1 mL solution of the gold colloids (15 nM) in water was mixed with excess (3.68:M) 5' epi-endrosterone linked-oligonucleotide (33 and 31 bases in length) in water, and the mixture was allowed to stand for 12-24 hours at room temperature. Then, 100 μL of a 0.1 M sodium hydrogen phosphate buffer, pH 7.0, and 100 μL of 1.0 M NaCl were premixed and added. After 10 minutes, 10 μL of 1% aqueous $NaN_3$ were added, and the mixture was allowed to stand for an additional 20 hours then increased the salt concentration to 0.3. After standing 4 h at 0.3 M NaCl again increased to 1M Nacl and kept further 16 h. This "aging" step was designed to increase the surface coverage by the epi disulfide linked-oligonucleotides and to displace oligonucleotide bases from the gold surface. Somewhat cleaner, better defined red spots in subsequent assays were obtained if the solution was frozen in a dry-ice bath after the 40-hour incubation and then thawed at room temperature. Either way, the solution was next centrifuged at 14,000 rpm in an Eppendorf Centrifuge 5414 for about 15 minutes to give a very pale pink supernatant containing most of the oligonucleotide (as indicated by the absorbance at 260 nm) along with 7-10% of the colloidal gold (as indicated by the absorbance at 520 nm), and a compact, dark, gelatinous residue at the bottom of the tube. The supernatant was removed, and the residue was resuspended in about 200 μL of buffer (10 mM phosphate, 0.1 M NaCl) and recentrifuged. After removal of the supernatant solution, the residue was taken up in 1.0 mL of buffer (10 mM phosphate, 0.1 M NaCl) and 10 μL of a 1% aqueous solution of $NaN_3$. Dissolution was assisted by drawing the solution into, and expelling it from, a pipette several times. The resulting red master solution was stable (i.e., remained red and did not aggregate) on standing for months at room temperature, on spotting on silica thin-layer chromatography (TLC) plates, and on addition to 2 M NaCl, 10 mM $MgCl_2$, or solutions containing high concentrations of salmon sperm DNA.

For examples 2-5 we prepared different set of Factor V probes using an aqueous solution of 17 nM (150 μL) Au colloids, as described above, was mixed with 3.75 μM (46 μL) 5'-epiendrosterone-$a_{20}$-tattcctcgcc (SEQ ID NO:2), and allowed to stand for 24 hours at room temperature in 1 ml Eppendorf capped vials. A second solution of colloids was reacted with 3.75 μM (46 μL) 5'-epiendrosterone-$a_{20}$-attcct-tgcct-3'. (SEQ ID NO:3). Note that these oligonucleotides are non-complementary. The residue was dissolved using the same procedure described above and the resulting solution was stored in a glass bottle until further use.

(e) Hybridization Conditions

Stock buffer solution: For the hybridization buffer, the following stock solution was used: 3.0 NaCl, 0.3 M Na-Citrate, 10 mM $MgCl_2$, 4.0 mM $NaH_2PO_4$ and 0.005% SDS.

Hybridization assay was performed using diluted buffer (0.78M NaCl, 70 mM sodium citate, 2.64 mM $MgCl_2$, 1.1 mM sodium phosphate, 0.01%) from the stock buffer solution by adding 0.5% of Tween. In a typical experiment procedure, target and probe were mixed with the hybridization buffer and heated the mixture at 95° C. for 5 minutes. After cooling to room temperature aliquots were transferred on to the glass substrate and placed in humidity chamber for hybridization (Different assays were done at different temperature conditions since each probe has a different melting temperature). After hybridization, plates were washed with two different wash buffers and spin dried. Plates dried were treated with silver amplification solutions (silverA+silverB) (silver amplification kit available from SIGMA, St. Louis, Mo. 63178, catalog no: S 5020 and S 5145) and the data was collected from the amplified plates using an imaging system for data collection described in (Nanosphere, Inc. assignee) U.S. patent application Ser. No. 10/210,959 and PCT/US02/24604, both filed Aug. 2, 2002, which are incorporated by reference in their entirety.

(f) Target Sequence Used

This Factor V target sequence was used in examples 2-6 for detection. M13 probes were used in example 1 for direct probe targeting to capture strand test the plates and no target detection was performed here. But from example 2-5 Factor V target detection was done in presence of Factor V probes and M13 probes. Here M13 probes served as controls. In plate no: 5 different combination of assay were performed on one plate including Factor V wild type and mismatch detection. Each well in plate no: 6 was clearly defined with target and probes used.

Factor V Wild Type Sequence:

```
5' gacatcgcctctgggctaataggactacttctaa  (SEQ ID NO:4)
tctgtaagagcagatccctggacaggcaaggaataca
ggtattttgtccttgaagtaacctttcag 3'
```

Probe Sequence:

```
Probe FV (13D):
5'-Epi-a20-tattcctcgcc 3'        (SEQ ID NO: 5)

Probe FV (26D):
5'-Epi-a20-attccttgcct3'         (SEQ ID NO: 6)
```

Capture Strand Sequence for Factor V Target Detection:

```
5'-tcc tga tga aga tta gac att ctc   (SEQ ID NO:7)
gtc-NH—CO—NH—Si-(OEt)3-3'
```

Stock buffer solution: For the hybridization buffer, the following stock solution was used: 3.0 NaCl, 0.3 M Na-Citrate, 10 mM $MgCl_2$, 4.0 mM $NaH_2PO_4$ and 0.005% SDS.

Example 3

Detection of M13 Target Sequence Using DNA Array Chip

Figure 6:
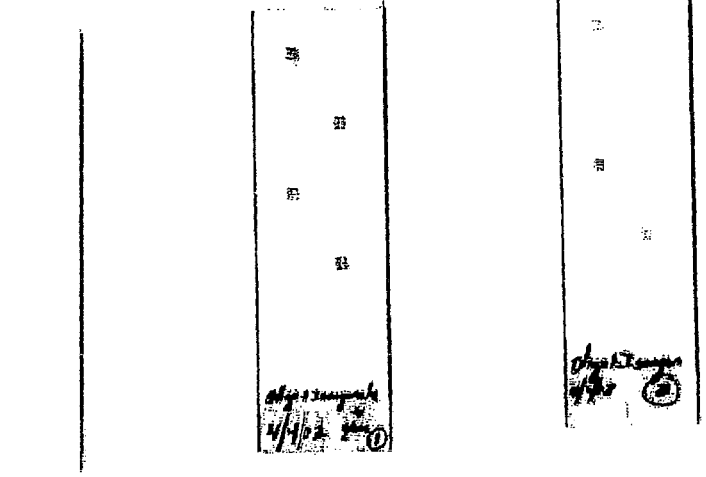
FIG. 6 illustrates the results of detection of M13 capture sequences using a DNA array chip prepared as described in Example 1 (method no. 1). In plate no. 1, a non-complementary nanoparticle-labeled oligonucleotide probe was used. In plates nos. 2 and 3, a specific complementary nanoparticle-labeled oligonucleotide probe was used. As expected, the plates using the specific complementary probes showed detection events. See Example 3.

In this Example, probe was targeted directly to the capture strand and a detection assay was performed. Plates Nos. 1-3 were prepared as described in Example 1 (method no. 1). In Plates 2 & 3, probes (FIG. 6) were clearly hybridized to the capture strand within 45 minutes. The gold colloid nanoparticles hybridized to the capture were clearly visible before silver amplification. In plate no 1 (FIG. 6), a different probe was used and the assay was developed to show the specificity. After silver stain development, signals were not shown on the glass surface even after silver amplification. This experiment established the specificity of the DNA chip prepared in accordance with the invention.

M13 Capture Sequence:

5'-tga aat tgt tat c-NH—CO—NH—Si—(OEt)$_3$-3'  (SEQ ID NO: 8)

Probe Used on Plates Nos. 2-3 Plates:

3'-act tta aca ata g-a$_{20}$-Epi-5'  (SEQ ID NO: 9)

On plate no. 1, a detection probe 3'-t taa cac tcg c-a$_{20}$-Epi-5' (SEQ ID NO:10) was used which was non-complementary to the capture strand for sequence specificity testing (no signals). This clearly showed the specificity of the both capture strand sequence and the probe. In both cases, 6 nM probe was used in diluted buffer conditions. In a typical experimental procedure, 30 µl of the diluted buffer (1.3M NaCl, 130 mM sodium citrate, 4.38 mM MgCl$_2$, 1.82 mM sodium phosphate, 0.003% SDS) and 20 µl of probe (10 nM) was flooded on the arrayed glass chip and allowed to hybridize for 1.5 h at room temperature. The final concentration of probe was 4 nM and buffer concentration was 0.78M NaCl, 70 mM sodium citrate, 2.64 mM MgCl$_2$, 1.1 mM sodium phosphate, 0.002% SDS. Thereafter, the chip was washed with 0.75 M sodium chloride, 75 mM citrate and 0.05% Tween buffer and then washed again with 0.5M sodium nitrate buffer. Then plates were treated with silver amplification solutions silverA+SilverB (1 mL+1 mL=total 2 mL) for 4 minutes and washed with nanopure water. Finally, the plates were exposed to the imaging system for data collection as discussed above.

Example 4

Detection of Factor V Target Sequence Using a DNA Array Chip

Figure 7:
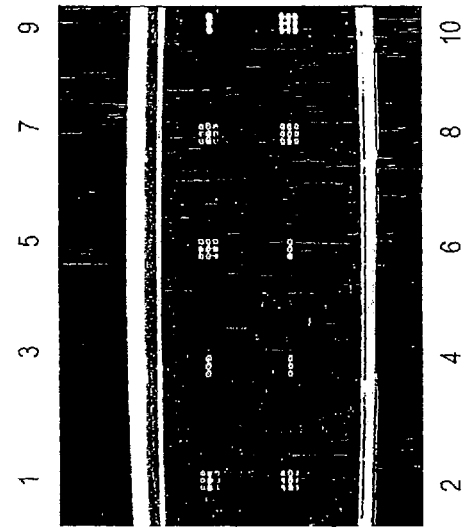
FIG. 7 illustrates the results of detection of Factor V target sequence using a sandwich hybridization assay. A DNA array chip was prepared as described in Example 1 (method no. 1) using Factor V capture probe. The DNA chip performed as expected. See Example 4.

In this Example, two different silanized capture strands were spotted directly on the plate and detected. The plate was prepared as described in Example 1 (method no. 1). The middle row always carried the positive control capture with other capture on top and bottom rows. Here, wild type, mutant and heterozygous samples were used for the detection. All samples were showed signals in the proper place using the above mentioned assay conditions. See FIG. 7.

a) Positive Controls Capture Sequence:

5'-tga aat tgt tat c-NH—CO—NH—Si—(OEt)$_3$-3'  (SEQ ID NO:10)

Probe Used was for Positive Control:

3'-act tta aca ata g-a$_{20}$-Epi-5'  (SEQ ID NO:11)

B) Probes Used for Target Detection are:

Probe FV 13D (probe for wild type target):
5'-Epi-a$_{20}$-tattcctcgcc 3'  (SEQ ID NO:12)

Probe FV 26D (probe for mutant target):
5'-Epi-a$_{20}$-attccttgcct3'  (SEQ ID NO:13)

Capture Strand Sequence for Factor V Target Detection:

5'-tcc tga tga aga tta gac att ctc gtc-NH—CO—NH—Si-(OEt)$_3$-3'

Factor V Wild Type Target Sequence:

5' gacatcgcctctgggctaataggactacttc (SEQ ID NO: 13)
taatctgtaagagcagatccctggacaggcaagg
aatacaggtattttgtccttgaagtaacctttca
g 3'

Mutant Factor V Target Sequence:

gtaggactacttctaatctgtaagagcagatccctg (SEQ ID NO:14)
gacaggtaaggaatacaggtattttgtccttgaagt
aacctttcag-3'

Heterozygous: 50% of Wild Type and 50% of Mutant Target.
Well 1: Heterozygous—Probe 26D was used
Well 2: Heterozygous—Probe 13D was used
Well 3: Control—with probe 26D, only positive control should show up
Well 4: Control—with probe13D, only positive control should show up
Well 5: Mutant—target with mutant probe 26D+positive control probe
Well 6: Mutant target—with wild type probe 13D+positive control
Well 7: Heterozygous—with probe 26D
Well 8: Heterozygous—with probe 13D
Well 9: Wild type target—with mutant probe 26D
Well 10: Wild type target—with wild type probe13D

Example 5

Detection of MTHFR Target Sequence on a DNA Array Plate

Figure 8:
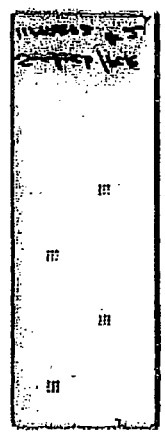
FIG. 8 illustrates the results of detection of MTHFR target sequence using a DNA array chip prepared as described in Example 1 (method no. 1). The DNA chip performed as expected. Plate No. 1 shows that the detection probe does not hybridized above its melting temperature. Plate No. 2 showed detection of a 100mer MTHFR synthetic target. Plate No. 3 showed detection of a MTHFR PCR product. See Example 5. See Example 5.
Figure 8:
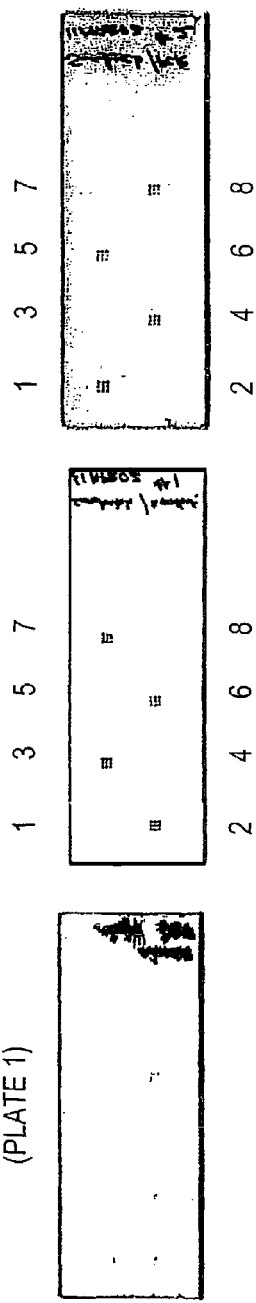

In this Example, an MTHFR 100mer synthetic target and 208 base pair PCR product (10 nM~50 nM) was used in the detection assay. The plates were prepared as described in Example 1 (method no. 1). Alternative wells were used as controls using M13 target and MTHFR 18mer probe and did not show even traces of silver, following silver signal amplification. As shown in plate no. 1 (FIG. 8), an experiment was performed at 70° C. to show that probe does not hybridize above melting temperature (MTHFR target and 18mer probe). The results show probe specificity and that at high temperature, the probes are not binding nonspecifically to the silyl oligo-attached substrate.

100mer Synthetic Target:

5'-aag cac ttg aag gag aag gtg tct (SEQ ID NO: 14)
gcg gga gcc gat ttc atc atc acg
cag ctt ttc ttt gag gct gac aca
ttc ttc cgc ttt gtg aag gca tgc
acc ga-3'

18mer Probe Sequence Used on all Three Plates:

```
3'-ctg tgt aag aag gcg ttt-A20-    (SEQ ID NO: 15)
Epi-5'
```

PCR Product: 208 Base Pair

```
5'ccttgaacaggtggaggccagcctctcctgactg (SEQ ID NO:16)
tcatccctattggcaggttaccccaaaggccacccc
gaagcagggagctttgaggctgacctgaagcacttg
aaggagaaggtgtctgcgggagccgatttcatcatc
acgcagcttttctttgaggctgacacattcttccgc
tttgtgaaggcatgcaccgacatgggcatcacttgc
cccatcgtccccgggatctttcccatccaggtgagg
ggcccaggagagcccataagctccctccaccccact
ctcaccgc
```

Experimental Conditions:

In a typical experimental procedure (on plate no: 2), to 30 µl of the diluted buffer (1.3M NaCl, 130 mM sodium citrate, 4.38 mM MgCl$_2$, 1.82 mM sodium phosphate, 0.003% SDS), 10 µl of 18mer probe (10 nM) and 2 µl of 100mer synthetic target (10 µM) 8 µl of water were mixed and flooded on the arrayed glass chip and allowed to hybridize for 1.5 h at room temperature. The final concentration of probe was 2 nM and target concentration was 400 pM and buffer concentration was 0.78M NaCl, 70 mM sodium citate, 2.64 mM MgCl$_2$, 1.1 mM sodium phosphate, 0.01%). After that washed with 0.75 M sodium chloride, 75 mM citrate and 0.05% Tween buffer and then washed again with 0.5M sodium nitrate buffer. After that plates were treated with silver A+SilverB (1 mL+1 mL=total 2 mL) (silver amplification kit available from SIGMA, St. Louis, Mo. 63178, catalog no: S 5020 and S 5145) for 4 minutes and washed with nanopure water. Finally plates were exposed to imaging system for data collection as discussed above. In Example 3 on plate no: 2, wells no: 2 1, 4, 5, 8 are controls and controls made up with M13 synthetic target and MTHFR 18mer probe (5'-tat gct tcc ggc tcg tat gtt gtg tgg aat tgt gag cgg ata aca att tca-3'). (SEQ ID NO: 17)

As mentioned earlier, the experiment on plate no. 1 (FIG. 8) was performed at 70° C. to show that above melting temperature probe 18mer probe did not bind to the capture probe.

Plate no. 3 (FIG. 8) was generated following the same experimental procedure and using the same probes. 10 µl (2 nm~10 nM) of MTHFR PCR product was used as target. Plate no. 3 wells 2, 3, 6 and 7 are the controls with Factor V 99mer mutant target and MTHFR 18mer probe.

Factor V 99mer Mutant Factor V Target Had the Following Sequence:

```
5'gtaggactacttctaatctgtaagagcagatc (SEQ ID NO: 18)
cctggacaggtaaggaatacaggtattttgtcct
tgaagtaacctttcag-3')
```

Example 6

Detection of Factor V Target Sequence on DNA Array Plate

Figure 9:
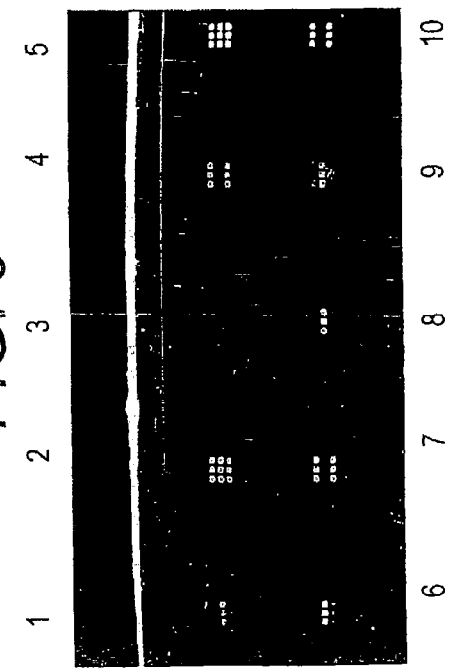
FIG. 9 illustrates the results of detection of Factor V target sequence using a DNA array chip prepared as described in Example 1 (method no. 1). The DNA chip performed as expected. No non-specific background noise was observed. See Example 6.

In this Example and in the following Example 7, the same capture strands were arrayed on the plate. The purpose of this experiment was to find out the difference in intensity of the spots after silver development when same oligomer was spotted on the slide at different places. Positive control was spotted in the middle of two Factor V 4G oligomer captures on the slide. The results are shown in FIG. 9.

Capture Strand Sequence for Factor V Target Detection was:

```
5' tcc tga tga aga tta gac att ctc    (SEQ ID NO:19)
gtc-NH—CO—NH—Si—(OEt)3-3'
```

Positive Capture Control Capture Spotted was (M13):

```
5' tga aat tgt tat c-NH—CO—NH—Si—     (SEQ ID NO:20)
(OEt)3-3'
```

The target sequence used was wild type Factor V 99base pair single strand DNA having the following sequence:

```
gtaggactacttctaatctgtaagagcagatccctg (SEQ ID NO:21)
gacaggcaaggaatacaggtattttgtccttgaagt
aacctttcag-3')
```

Mutant Factor V target had the following sequence:

```
gtaggactacttctaatctgtaagagcagatccctg (SEQ ID NO:22)
gacaggtaaggaatacaggtattttgtccttgaagt
aacctttcag-3')
``` and probes used had the following sequence:

```
probe FV 13D:
  5'-Epi-a20-tattcctcgcc 3',         (SEQ ID NO:23)

probe FV 26D:
  5'-Epi-a20-attccttgcct3'.          (SEQ ID NO:24)
```

```
Capture Strand Sequence for factor V
target detection:
5'-tcc tga tga aga tta gac att ctc    (SEQ ID NO:25)
gtc-NH—CO—NH—Si—(OEt)3-3'

Positive control sequence:
5'-tga aat tgt tat c-NH2-3'           (SEQ ID NO:26)

and probe used for positive control
was:
3'-act tta aca ata g-a20-Epi-5'       (SEQ ID NO:27)
```

In a typical experimental procedure, to 25 µl of the diluted buffer (1.3M NaCl, 130 mM sodium citrate, 4.38 mM MgCl$_2$, 1.82 mM sodium phosphate, 0.003% SDS), 10 µl of probe (10 nM) and 10 µl of PCR target (15-50 nM) and 5 µl of positive control probe (10 nM) were mixed and flooded on the arrayed glass chip and allowed to hybridize for 1.5 h at room temperature. The final concentration of probe was 2 nM, and buffer concentration was 0.78M NaCl, 70 mM sodium citate, 2.64 mM MgCl$_2$, 1.1 mM sodium phosphate, 0.01%). that the plates was then washed with 0.75 Sodium chloride, 75 mM citrate and 0.05% tween buffer and then washed again with 0.5M Sodium Nitrate buffer. The plates were treated with silver A+SilverB (1 mL+1 mL=total 2 mL) for 4 minutes and washed with nanopure water. Finally, the plates were exposed to the imaging system described above for data collection. Both positive control probe and target reacted probe were mixed and the assay was run to show the selectivity of the probe. The wells were identified as follows:

Wells 1, 6, 8 and 9 have only positive control probe with target and buffer.

Wells 2, 5 had both positive control probe and target probe with targets and buffer.

Wells 4, 7 and 10 have only target probe with target and buffer and here positive control probe and target were absent.

Well 3 did not have any target and positive control probe but it had target probe and buffer.

These results (FIG. 9) show that probes were specific to target detection and no non-specific background noise was observed when target was absent.

Example 7

Detection of Factor V Target Sequence

Figure 10:
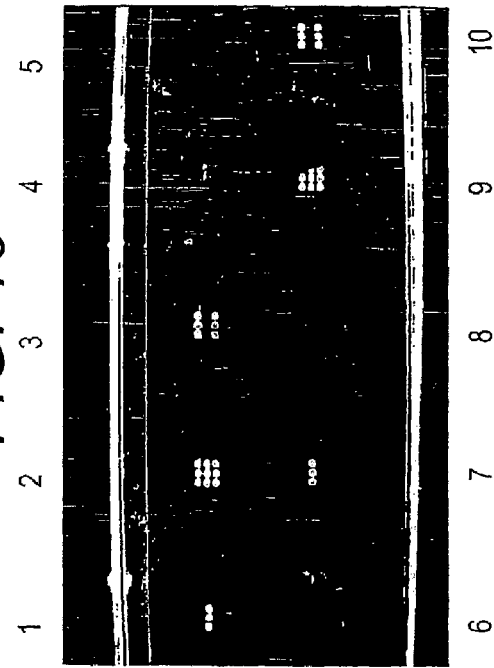
FIG. 10 illustrates the results of detection of Factor V target sequence using a DNA array chip prepared as described in Example 1 (method no. 1). The DNA chip performed as expected. The probes reacted specifically to the target sequence and no cross-hybridization between the probes and targets was observed. See Example 7.

In this Example, all capture strands pattern is the same as described in Example no. 6. Moreover, the same experimental conditions and concentrations described in Example 6 were used to perform the assay at 52° C. Wild type and mutant targets were given in the example 6. The results are shown in FIG. 10. The wells are identified as follows:

Well 1: Positive control probe directly probing to the capture strand in the same buffer conditions mentioned in example 4.

Well 2: Factor V Probe 5'-Epi-$a_{20}$-attccttgcct-3' (26D) (SEQ ID NO: 27) and Factor V 99base pair mutant target, positive control probe and buffer.

Well 3: Factor V Probe 5'-Epi-$a_{20}$-attccttgcct-3' (26D) (SEQ ID NO: 28) and Factor V 99base pair mutant target and hybridization buffer.

Well 4: Probe 13D and Factor V mutant PCR target, positive control and hybridization buffer.

Well 5: Probe 13D and Factor V mutant PCR target, and hybridization buffer.

Well 6: Control (MTHFR target and Probe 13D and hybridization buffer).

Well 7: Wild type Factor V target, probe (26D), positive control probe and hybridization buffer, Well 8: Wild type Factor V target and probe (26D), and hybridization buffer.

Well 9: Wild type Factor V target, probe 13(D), positive control probe and hybridization buffer.

Well 10: Wild type Factor V target, probe 13(D), and hybridization buffer.

```
Probe FV 13D:
    5'-Epi-a₂₀-tattcctcgcc-3'        (SEQ ID NO: 29)

Probe FV 26D:
    5'-Epi-a₂₀-attccttgcct-3'        (SEQ ID NO: 30)
```

These results (FIG. 10) show that probes were reacted specifically to the target and there is no cross hybridization between probes and targets were observed when probes were mixed with different targets.

REFERENCES

1. *Nucleic Acids research*, vol 22, 5456-5465 (1994).
2. *Nucleic Acids research*, vol 24, 3040-3047 (1996).
3. *Nucleic Acids research*, vol 24, 3031-3039(1996).
4. *Nucleic Acids research*, vol 27, 1970-1977 (1999).
5. *Angew. Chem. Int. Ed*, 38, No. 9, 1297(1999)
6. *Analytical biochemistry* 280, 143-150 (2000).
7. (a) *Nucleic Acids research, vol.* 28, No. 13 E71 (2000);
    (b) Huber et al. WO 01/46214, published Jun. 28, 2001
    (c) Huber et al. WO 01/46213, published Jun. 28, 2001
    (d) Huber et al. WO 01/46464, published Jun. 28, 2001
8. *Nucleic Acids research*, vol 29, 955-959 (2001).
9. *Nucleic Acids research*, vol 29, No. 13 e69 (2001).
10. *Bioconjugate Chemistry*, 2000, 11, 289-291

---

What is claimed:

1. A compound having a formula vi:

$$[(R_1)(R_2)(R_3)Si-X-Z-CYNH]_2-Si\ (NCY)_2 \qquad vi$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy.

2. The compound of claim 1 wherein $R_1$, $R_2$ and $R_3$ represents methoxy, X represents phenyl, Y represents oxygen, and Z represents NH.

3. A kit comprising:
a container comprising a compound having the formula vi:

$$[(R_1)(R_2)(R_3)Si-X-Z-CYNH]_2-Si\ (NCY)_2 \qquad vi$$

wherein $R_1$, $R_2$ and $R_3$ independently represents $C_1$-$C_6$ alkoxy, $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, or sulfur; Y represents oxygen or sulfur; and Z represents oxygen or NH, with the proviso that at least one of $R_1$, $R_2$, or $R_3$ represents $C_1$-$C_6$ alkoxy; and an optional substrate.

4. The kit of claim 3 wherein $R_1$, $R_2$ and $R_3$ represents methoxy, X represents phenyl, Y represents oxygen, and Z represents NH.

* * * * *

SEQUENCE LISTING

```
<160> NUMBER OF SEQ ID NOS: 14

<210> SEQ ID NO 1
<211> LENGTH: 34
<212> TYPE: DNA
<213> ORGANISM: artificial
<220> FEATURE:
<223> OTHER INFORMATION: probe
<220> FEATURE:
<221> NAME/KEY: misc_feature
<222> LOCATION: (1)..(1)
<223> OTHER INFORMATION: n = epiendrosterone

<400> SEQUENCE: 1
naaaaaaaaa aaaaaaaaaa agataacaat ttca                             34

<210> SEQ ID NO 2
<211> LENGTH: 32
<212> TYPE: DNA
<213> ORGANISM: artificial
<220> FEATURE:
<223> OTHER INFORMATION: probe
<220> FEATURE:
<221> NAME/KEY: misc_feature
<222> LOCATION: (1)..(1)
<223> OTHER INFORMATION: n = epiendrosterone

<400> SEQUENCE: 2
```
naaaaaaaaa aaaaaaaaaa acgctcacaa tt                                    32

<210> SEQ ID NO 3
<211> LENGTH: 32
<212> TYPE: DNA
<213> ORGANISM: artificial
<220> FEATURE:
<223> OTHER INFORMATION: Probe FV (13D)
<220> FEATURE:
<221> NAME/KEY: misc_feature
<222> LOCATION: (1)..(1)
<223> OTHER INFORMATION: n = epiendrosterone

<400> SEQUENCE: 3
naaaaaaaaa aaaaaaaaaa atattcctcg cc                                    32

<210> SEQ ID NO 4
<211> LENGTH: 32
<212> TYPE: DNA
<213> ORGANISM: artificial
<220> FEATURE:
<223> OTHER INFORMATION: Probe FV (26D)
<220> FEATURE:
<221> NAME/KEY: misc_feature
<222> LOCATION: (1)..(1)
<223> OTHER INFORMATION: n = epiendrosterone

<400> SEQUENCE: 4
naaaaaaaaa aaaaaaaaaa aattccttgc ct                                    32

<210> SEQ ID NO 5
<211> LENGTH: 100
<212> TYPE: DNA
<213> ORGANISM: artificial
<220> FEATURE:
<223> OTHER INFORMATION: Factor V wild type sequence

<400> SEQUENCE: 5
gacatcgcct ctgggctaat aggactactt ctaatctgta agagcagatc cctggacagg       60
caaggaatac aggtattttg tccttgaagt aacctttcag                            100

<210> SEQ ID NO 6
<211> LENGTH: 28
<212> TYPE: DNA
<213> ORGANISM: artificial
<220> FEATURE:
<223> OTHER INFORMATION: Capture Strand Sequence For factor V target
      detection
<220> FEATURE:
<221> NAME/KEY: misc_feature
<222> LOCATION: (28)..(28)
<223> OTHER INFORMATION: NH-CO-NH- Si-(OEt)3

<400> SEQUENCE: 6
tcctgatgaa gattagacat tctcgtcn                                         28

<210> SEQ ID NO 7
<211> LENGTH: 14
<212> TYPE: DNA
<213> ORGANISM: artificial
<220> FEATURE:
<223> OTHER INFORMATION: M13 Capture sequence
<220> FEATURE:
<221> NAME/KEY: misc_feature
<222> LOCATION: (14)..(14)
<223> OTHER INFORMATION: NH-CO-NH-- Si-(OEt)3

<400> SEQUENCE: 7
tgaaattgtt atcn                                                        14

<210> SEQ ID NO 8
<211> LENGTH: 82
<212> TYPE: DNA
<213> ORGANISM: artificial
<220> FEATURE:
<223> OTHER INFORMATION: Mutant Factor V target sequence

<400> SEQUENCE: 8
gtaggactac ttctaatctg taagagcaga tccctggaca ggtaaggaat acaggtattt      60
tgtccttgaa gtaacctttc ag                                               82

<210> SEQ ID NO 9
<211> LENGTH: 101
<212> TYPE: DNA
<213> ORGANISM: artificial
<220> FEATURE:
<223> OTHER INFORMATION: synthetic oligonucleotide

<400> SEQUENCE: 9
aagcacttga aggagaaggt gtctgcggga gccgatttca tcatcacgca gcttttcttt      60
gaggctgaca cattcttccg ctttgtgaag gcatgcaccg a                         101

<210> SEQ ID NO 10
<211> LENGTH: 39
<212> TYPE: DNA
<213> ORGANISM: artificial
<220> FEATURE:
<223> OTHER INFORMATION: probe
<220> FEATURE:
<221> NAME/KEY: misc_feature
<222> LOCATION: (1)..(1)
<223> OTHER INFORMATION: n = epiendrosterone

<400> SEQUENCE: 10
naaaaaaaaa aaaaaaaaaa atttgcggaa gaatgtgtc                             39

<210> SEQ ID NO 11
<211> LENGTH: 294
<212> TYPE: DNA
<213> ORGANISM: artificial
<220> FEATURE:
<223> OTHER INFORMATION: synthetic oligonucleotide

<400> SEQUENCE: 11
ccttgaacag gtggaggcca gcctctcctg actgtcatcc ctattggcag gttaccccaa      60
aggccacccc gaagcaggga gctttgaggc tgacctgaag cacttgaagg agaaggtgtc     120
tgcgggagcc gatttcatca tcacgcagct tttctttgag gctgacacat tcttccgctt     180
tgtgaaggca tgcaccgaca tgggcatcac ttgccccatc gtccccggga tctttcccat     240
ccaggtgagg ggcccaggag agcccataag ctccctccac cccactctca ccgc           294

<210> SEQ ID NO 12
<211> LENGTH: 51
<212> TYPE: DNA
<213> ORGANISM: artificial
<220> FEATURE:
<223> OTHER INFORMATION: MTHFR probe

<400> SEQUENCE: 12
tatgcttccg gctcgtatgt tgtgtggaat tgtgagcgga taacaatttc a                51

```
<210> SEQ ID NO 13
<211> LENGTH: 82
<212> TYPE: DNA
<213> ORGANISM: artificial
<220> FEATURE:
<223> OTHER INFORMATION: synthetic oligonucleotide

<400> SEQUENCE: 13
gtaggactac ttctaatctg taagagcaga tccctggaca ggcaaggaat acaggtattt      60
tgtccttgaa gtaacctttc ag                                              82

<210> SEQ ID NO 14
<211> LENGTH: 14
<212> TYPE: DNA
<213> ORGANISM: artificial
<220> FEATURE:
<223> OTHER INFORMATION: synthetic oligonucleotide
<220> FEATURE:
<221> NAME/KEY: misc_feature
<222> LOCATION: (14)..(14)
<223> OTHER INFORMATION: n = NH2

<400> SEQUENCE: 14
tgaaattgtt atcn                                                       14
```